US008343093B2

(12) United States Patent
Rush

(10) Patent No.: US 8,343,093 B2
(45) Date of Patent: *Jan. 1, 2013

(54) FLUID DELIVERY DEVICE WITH AUTOCALIBRATION

(75) Inventor: Benjamin M. Rush, Oakland, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/790,733

(22) Filed: May 28, 2010

(65) Prior Publication Data

US 2010/0312177 A1 Dec. 9, 2010

Related U.S. Application Data

(63) Continuation of application No. 11/105,711, filed on Apr. 13, 2005, now Pat. No. 7,727,181, which is a continuation-in-part of application No. 10/683,659, filed on Oct. 9, 2003, now Pat. No. 6,916,159.

(60) Provisional application No. 60/424,613, filed on Nov. 6, 2002, provisional application No. 60/417,434, filed on Oct. 9, 2002.

(51) Int. Cl.
*A61M 31/00* (2006.01)
(52) U.S. Cl. ........................................................ 604/67
(58) Field of Classification Search .............. 604/65, 604/67, 131, 134, 135, 151, 152, 153, 154, 604/155
See application file for complete search history.

(56) References Cited

U.S. PATENT DOCUMENTS

| | | | |
|---|---|---|---|
| 2,508,253 | A | 5/1950 | Haggardt |
| 2,915,579 | A | 12/1959 | Mendelsohn |
| 3,374,337 | A | 3/1968 | Burley |
| 3,510,747 | A | 5/1970 | Petrides |
| 3,541,892 | A | 11/1970 | Kubinek et al. |
| 3,606,592 | A | 9/1971 | Madurski et al. |
| 3,750,687 | A | 8/1973 | Williams |
| 3,843,455 | A | 10/1974 | Bier |
| 3,923,060 | A | 12/1975 | Ellinwood |
| 3,930,493 | A | 1/1976 | Williamson |
| 3,938,140 | A | 2/1976 | Garcia et al. |

(Continued)

FOREIGN PATENT DOCUMENTS
EP 0455455 11/1991
(Continued)

OTHER PUBLICATIONS

"An Electrochemical Slow Flow Meter", http://gore.ocean.washington.edu/research/slow_flow_meter.html, 2005, 3 pages.

(Continued)

*Primary Examiner* — Nicholas Lucchesi
*Assistant Examiner* — Aarti B Berdichevsky
(74) *Attorney, Agent, or Firm* — Jackson & Co., LLP

(57) ABSTRACT

A micro fluid delivery device is particularly useful in medical applications. The device may be worn or carried by the user and may deliver drugs or other medicaments to the user or patient. The device has a control system that accepts input from the user and controls all aspects of operation of the device. The control system measures the output of the pump and adjusts the output of the pump to achieve the desired dosage rate and size. This eliminates differences from pump to pump that result from inevitable variations in the manufacturing of such small scale affordable devices.

16 Claims, 6 Drawing Sheets

U.S. PATENT DOCUMENTS

| | | |
|---|---|---|
| 3,994,799 A | 11/1976 | Yao et al. |
| 4,018,547 A | 4/1977 | Rogen |
| 4,048,551 A | 9/1977 | Bosik |
| 4,121,282 A | 10/1978 | Ohsawa |
| 4,146,029 A | 3/1979 | Ellinwood |
| 4,193,397 A | 3/1980 | Tucker et al. |
| 4,268,173 A | 5/1981 | Barnard et al. |
| 4,288,793 A | 9/1981 | Lotscher |
| 4,309,156 A | 1/1982 | Gonner et al. |
| 4,362,052 A | 12/1982 | Heath et al. |
| 4,401,122 A | 8/1983 | Clark, Jr. |
| 4,439,197 A | 3/1984 | Honda et al. |
| 4,441,968 A | 4/1984 | Emmer et al. |
| 4,447,224 A | 5/1984 | DeCant, Jr. et al. |
| 4,458,686 A | 7/1984 | Clark, Jr. |
| 4,467,811 A | 8/1984 | Clark, Jr. |
| 4,472,113 A | 9/1984 | Rogen |
| 4,474,309 A | 10/1984 | Solomon |
| 4,486,190 A | 12/1984 | Reinicke |
| 4,494,950 A | 1/1985 | Fischell |
| 4,512,348 A | 4/1985 | Uchigaki et al. |
| 4,524,343 A | 6/1985 | Morgan et al. |
| 4,529,401 A | 7/1985 | Leslie et al. |
| 4,531,235 A | 7/1985 | Brusen |
| 4,562,751 A | 1/1986 | Nason et al. |
| 4,563,249 A | 1/1986 | Hale |
| 4,570,492 A | 2/1986 | Walsh |
| 4,573,994 A | 3/1986 | Fischell et al. |
| 4,574,809 A | 3/1986 | Talish et al. |
| 4,633,878 A | 1/1987 | Bombardieri |
| 4,678,408 A | 7/1987 | Nason et al. |
| 4,685,903 A | 8/1987 | Cable et al. |
| 4,686,624 A | 8/1987 | Blum et al. |
| 4,736,748 A | 4/1988 | Nakamura et al. |
| 4,755,173 A | 7/1988 | Konopka et al. |
| 4,811,564 A | 3/1989 | Palmer |
| 4,850,959 A | 7/1989 | Findl |
| 4,851,827 A | 7/1989 | Nicholas |
| 4,866,396 A | 9/1989 | Tamura |
| 4,883,409 A | 11/1989 | Strohmeier et al. |
| 4,890,621 A | 1/1990 | Hakky |
| 4,953,552 A | 9/1990 | DeMarzo |
| 4,976,590 A | 12/1990 | Baldwin |
| 4,979,509 A | 12/1990 | Hakky |
| 4,984,581 A | 1/1991 | Stice |
| 5,004,532 A | 4/1991 | Hale et al. |
| 5,012,667 A | 5/1991 | Kruse |
| 5,019,974 A | 5/1991 | Beckers |
| 5,036,861 A | 8/1991 | Sembrowich et al. |
| 5,051,880 A | 9/1991 | Harm et al. |
| 5,061,914 A | 10/1991 | Busch et al. |
| 5,078,683 A | 1/1992 | Sancoff et al. |
| 5,079,920 A | 1/1992 | Whitehead et al. |
| 5,081,421 A | 1/1992 | Miller et al. |
| 5,101,814 A | 4/1992 | Palti |
| 5,124,661 A | 6/1992 | Zelin et al. |
| 5,139,023 A | 8/1992 | Stanley et al. |
| 5,155,695 A | 10/1992 | Stein |
| 5,190,041 A | 3/1993 | Palti |
| 5,205,819 A | 4/1993 | Ross et al. |
| 5,207,666 A | 5/1993 | Idriss et al. |
| 5,211,371 A | 5/1993 | Coffee |
| 5,211,626 A | 5/1993 | Frank et al. |
| 5,223,822 A | 6/1993 | Stommes et al. |
| 5,262,305 A | 11/1993 | Heller et al. |
| 5,264,104 A | 11/1993 | Gregg et al. |
| 5,267,026 A | 11/1993 | Kawahara et al. |
| 5,278,997 A | 1/1994 | Martin |
| 5,284,423 A | 2/1994 | Holdsworth et al. |
| 5,284,425 A | 2/1994 | Holtermann et al. |
| 5,291,614 A | 3/1994 | Baker et al. |
| 5,291,887 A | 3/1994 | Stanley et al. |
| 5,320,725 A | 6/1994 | Gregg et al. |
| 5,324,599 A | 6/1994 | Oyama et al. |
| 5,325,280 A | 6/1994 | Tortola et al. |
| 5,349,852 A | 9/1994 | Kamen et al. |
| 5,356,786 A | 10/1994 | Heller et al. |
| 5,366,292 A | 11/1994 | Voss |
| 5,368,028 A | 11/1994 | Palti |
| 5,371,687 A | 12/1994 | Holmes, II et al. |
| 5,372,133 A | 12/1994 | Hogen Esch |
| 5,376,070 A | 12/1994 | Purvis et al. |
| 5,382,331 A | 1/1995 | Banks |
| 5,390,671 A | 2/1995 | Lord et al. |
| 5,391,250 A | 2/1995 | Cheney, II et al. |
| 5,398,681 A | 3/1995 | Kupershmidt |
| 5,404,585 A | 4/1995 | Vimpari et al. |
| 5,406,301 A | 4/1995 | Ravid |
| 5,445,611 A | 8/1995 | Eppstein et al. |
| 5,448,992 A | 9/1995 | Kupershmidt |
| 5,458,140 A | 10/1995 | Eppstein et al. |
| 5,469,025 A | 11/1995 | Kanemori et al. |
| 5,479,486 A | 12/1995 | Saji |
| 5,494,562 A | 2/1996 | Maley et al. |
| 5,497,772 A | 3/1996 | Schulman et al. |
| 5,505,713 A | 4/1996 | Van Antwerp |
| 5,507,288 A | 4/1996 | Bocker et al. |
| 5,515,390 A | 5/1996 | Benton |
| 5,517,434 A | 5/1996 | Hanson et al. |
| 5,526,844 A | 6/1996 | Kamen et al. |
| 5,533,389 A | 7/1996 | Kamen et al. |
| 5,543,678 A | 8/1996 | Hoiberg |
| 5,559,528 A | 9/1996 | Ravid |
| 5,568,400 A | 10/1996 | Stark et al. |
| 5,568,806 A | 10/1996 | Cheney, II et al. |
| 5,573,506 A | 11/1996 | Vasko |
| 5,575,770 A | 11/1996 | Melsky et al. |
| 5,576,535 A | 11/1996 | Oosterwijk et al. |
| 5,586,553 A | 12/1996 | Halili et al. |
| 5,593,852 A | 1/1997 | Heller et al. |
| 5,594,906 A | 1/1997 | Holmes, II et al. |
| 5,596,261 A | 1/1997 | Suyama |
| 5,601,435 A | 2/1997 | Quy |
| 5,604,404 A | 2/1997 | Sahara |
| 5,615,671 A | 4/1997 | Schoonen et al. |
| 5,622,413 A | 4/1997 | Kim et al. |
| 5,622,482 A | 4/1997 | Lee |
| 5,640,954 A | 6/1997 | Pfeiffer et al. |
| 5,645,709 A | 7/1997 | Birch et al. |
| 5,660,163 A | 8/1997 | Schulman et al. |
| 5,661,643 A | 8/1997 | Blakely et al. |
| 5,662,461 A | 9/1997 | Ono |
| 5,665,222 A | 9/1997 | Heller et al. |
| 5,671,301 A | 9/1997 | Kupershmidt |
| 5,685,844 A | 11/1997 | Marttila |
| 5,695,949 A | 12/1997 | Galen et al. |
| 5,703,928 A | 12/1997 | Galloway et al. |
| 5,707,502 A | 1/1998 | McCaffrey et al. |
| 5,708,247 A | 1/1998 | McAleer et al. |
| 5,711,861 A | 1/1998 | Ward et al. |
| 5,711,868 A | 1/1998 | Maley et al. |
| 5,722,397 A | 3/1998 | Eppstein |
| 5,738,220 A | 4/1998 | Geszler |
| 5,741,211 A | 4/1998 | Renirie et al. |
| 5,748,872 A | 5/1998 | Norman |
| 5,759,510 A | 6/1998 | Pillai |
| 5,771,890 A | 6/1998 | Tamada |
| 5,774,254 A | 6/1998 | Berlin |
| 5,786,439 A | 7/1998 | Van Antwerp et al. |
| 5,790,297 A | 8/1998 | Berlin |
| 5,791,344 A | 8/1998 | Schulman et al. |
| 5,812,102 A | 9/1998 | Sprole et al. |
| 5,814,020 A | 9/1998 | Gross |
| 5,814,599 A | 9/1998 | Mitragotri et al. |
| 5,815,303 A | 9/1998 | Berlin |
| 5,822,715 A | 10/1998 | Worthington et al. |
| 5,825,488 A | 10/1998 | Kohl et al. |
| 5,848,990 A | 12/1998 | Cirelli et al. |
| 5,851,197 A | 12/1998 | Marano et al. |
| 5,856,631 A | 1/1999 | Julien |
| 5,858,001 A | 1/1999 | Tsals et al. |
| 5,873,026 A | 2/1999 | Reames |
| 5,875,417 A | 2/1999 | Golden |
| 5,885,211 A | 3/1999 | Eppstein et al. |
| 5,899,855 A | 5/1999 | Brown |
| 5,913,833 A | 6/1999 | Elstrom et al. |
| 5,918,603 A | 7/1999 | Brown |

| | | | | | | |
|---|---|---|---|---|---|---|
| 5,919,167 | A | 7/1999 | Mulhauser | 6,232,370 B1 | 5/2001 | Kubota et al. |
| 5,923,512 | A | 7/1999 | Brownlow et al. | 6,233,471 B1 | 5/2001 | Berner et al. |
| 5,931,814 | A | 8/1999 | Alex et al. | 6,233,539 B1 | 5/2001 | Brown |
| 5,947,921 | A | 9/1999 | Johnson et al. | 6,242,961 B1 | 6/2001 | Liu et al. |
| 5,948,512 | A | 9/1999 | Kubota et al. | 6,245,060 B1 | 6/2001 | Loomis et al. |
| 5,951,582 | A | 9/1999 | Thorne et al. | 6,248,067 B1 | 6/2001 | Causey, III et al. |
| 5,951,836 | A | 9/1999 | McAleer et al. | 6,262,708 B1 | 7/2001 | Chu |
| 5,954,643 | A | 9/1999 | VanAntwerp et al. | 6,272,364 B1 | 8/2001 | Kurnik |
| 5,965,380 | A | 10/1999 | Heller et al. | 6,278,425 B1 | 8/2001 | DeLuca |
| 5,968,011 | A | 10/1999 | Larsen et al. | 6,280,587 B1 | 8/2001 | Matsumoto |
| 5,971,922 | A | 10/1999 | Arita et al. | 6,283,926 B1 | 9/2001 | Cunningham et al. |
| 5,972,199 | A | 10/1999 | Heller et al. | 6,283,951 B1 | 9/2001 | Flaherty et al. |
| 5,993,411 | A | 11/1999 | Choi | 6,284,478 B1 | 9/2001 | Heller et al. |
| 5,994,878 | A | 11/1999 | Ostergaard et al. | 6,288,653 B1 | 9/2001 | Shih |
| 5,997,501 | A | 12/1999 | Gross et al. | 6,293,925 B1 | 9/2001 | Safabash et al. |
| 6,001,067 | A | 12/1999 | Shults et al. | 6,295,506 B1 | 9/2001 | Heinonen et al. |
| 6,002,961 | A | 12/1999 | Mitragotri et al. | 6,298,254 B2 | 10/2001 | Tamada |
| 6,011,486 | A | 1/2000 | Casey | 6,298,255 B1 | 10/2001 | Cordero et al. |
| 6,014,577 | A | 1/2000 | Henning et al. | 6,299,578 B1 | 10/2001 | Kurnik et al. |
| 6,017,328 | A | 1/2000 | Fischell et al. | 6,301,499 B1 | 10/2001 | Carlson et al. |
| 6,018,678 | A | 1/2000 | Mitragotri et al. | 6,306,104 B1 | 10/2001 | Cunningham et al. |
| 6,023,629 | A | 2/2000 | Tamada | 6,309,351 B1 | 10/2001 | Kurnik et al. |
| 6,024,539 | A | 2/2000 | Blomquist | 6,312,888 B1 | 11/2001 | Wong et al. |
| 6,026,320 | A | 2/2000 | Carlson et al. | 6,315,721 B2 | 11/2001 | Schulman et al. |
| 6,027,459 | A | 2/2000 | Shain et al. | 6,326,160 B1 | 12/2001 | Dunn et al. |
| 6,027,496 | A | 2/2000 | Loomis et al. | 6,329,161 B1 | 12/2001 | Heller et al. |
| 6,027,692 | A | 2/2000 | Galen et al. | 6,331,244 B1 | 12/2001 | Lewis et al. |
| 6,032,059 | A | 2/2000 | Henning et al. | 6,338,790 B1 | 1/2002 | Feldman et al. |
| 6,041,253 | A | 3/2000 | Kost et al. | 6,341,232 B1 | 1/2002 | Conn et al. |
| 6,041,665 | A | 3/2000 | Hussain | 6,356,776 B1 | 3/2002 | Berner et al. |
| 6,059,546 | A | 5/2000 | Brenan et al. | 6,360,888 B1 | 3/2002 | McIvor et al. |
| 6,063,039 | A | 5/2000 | Cunningham et al. | 6,366,793 B1 | 4/2002 | Bell et al. |
| 6,064,368 | A | 5/2000 | Kang | 6,368,141 B1 | 4/2002 | VanAntwerp et al. |
| 6,066,243 | A | 5/2000 | Anderson et al. | 6,368,274 B1 | 4/2002 | Van Antwerp et al. |
| 6,067,017 | A | 5/2000 | Stewart et al. | 6,372,371 B1 | 4/2002 | Iarochenko et al. |
| 6,067,463 | A | 5/2000 | Jeng et al. | 6,375,344 B1 | 4/2002 | Hanson et al. |
| 6,071,249 | A | 6/2000 | Cunningham et al. | 6,375,638 B2 | 4/2002 | Nason et al. |
| 6,071,251 | A | 6/2000 | Cunningham et al. | 6,377,894 B1 | 4/2002 | Deweese et al. |
| 6,073,031 | A | 6/2000 | Helstab et al. | 6,379,301 B1 | 4/2002 | Worthington et al. |
| 6,077,660 | A | 6/2000 | Wong et al. | 6,381,496 B1 | 4/2002 | Meadows et al. |
| 6,081,104 | A | 6/2000 | Kern | 6,393,318 B1 | 5/2002 | Conn et al. |
| 6,083,710 | A | 7/2000 | Heller et al. | 6,403,944 B1 | 6/2002 | MacKenzie et al. |
| 6,085,871 | A | 7/2000 | Karamata | 6,405,066 B1 | 6/2002 | Essenpreis et al. |
| 6,086,575 | A | 7/2000 | Mejslov | 6,408,402 B1 | 6/2002 | Norman |
| 6,091,975 | A | 7/2000 | Daddona et al. | 6,417,074 B2 | 7/2002 | Kopley et al. |
| 6,093,156 | A | 7/2000 | Cunningham et al. | 6,418,332 B1 | 7/2002 | Mastrototaro et al. |
| 6,093,172 | A | 7/2000 | Funderburk et al. | 6,419,642 B1 | 7/2002 | Marchitto et al. |
| 6,103,033 | A | 8/2000 | Say et al. | 6,425,829 B1 | 7/2002 | Julien |
| 6,120,676 | A | 9/2000 | Heller et al. | 6,427,088 B1 | 7/2002 | Bowman, IV et al. |
| 6,121,009 | A | 9/2000 | Heller et al. | 6,432,585 B1 | 8/2002 | Kawakami et al. |
| 6,129,823 | A | 10/2000 | Hughes et al. | 6,437,379 B2 | 8/2002 | Kopley et al. |
| 6,132,371 | A | 10/2000 | Dempsey et al. | 6,438,385 B1 | 8/2002 | Heinonen et al. |
| 6,134,461 | A | 10/2000 | Say et al. | 6,438,414 B1 | 8/2002 | Conn et al. |
| 6,142,939 | A | 11/2000 | Eppstein et al. | 6,442,413 B1 | 8/2002 | Silver |
| 6,143,164 | A | 11/2000 | Heller et al. | 6,445,374 B2 | 9/2002 | Albert et al. |
| 6,144,303 | A | 11/2000 | Federman | 6,461,329 B1 | 10/2002 | Van Antwerp et al. |
| 6,144,869 | A | 11/2000 | Berner et al. | 6,462,162 B2 | 10/2002 | Van Antwerp et al. |
| 6,144,922 | A | 11/2000 | Douglas et al. | 6,464,848 B1 | 10/2002 | Matsumoto |
| 6,147,342 | A | 11/2000 | Kucher | 6,466,807 B1 | 10/2002 | Dobson et al. |
| 6,154,855 | A | 11/2000 | Norman | 6,466,810 B1 | 10/2002 | Ward et al. |
| 6,155,992 | A | 12/2000 | Henning et al. | 6,468,222 B1 | 10/2002 | Mault et al. |
| 6,157,442 | A | 12/2000 | Raskas | 6,471,980 B2 | 10/2002 | Sirhan et al. |
| 6,160,449 | A | 12/2000 | Klomsdorf et al. | 6,472,991 B1 | 10/2002 | Schulman et al. |
| 6,162,202 | A | 12/2000 | Sicurelli et al. | 6,475,196 B1 | 11/2002 | Vachon |
| 6,162,611 | A | 12/2000 | Heller et al. | 6,478,736 B1 | 11/2002 | Mault |
| 6,164,284 | A | 12/2000 | Schulman et al. | 6,480,730 B2 | 11/2002 | Darrow et al. |
| 6,173,160 | B1 | 1/2001 | Liimatainen | 6,482,158 B2 | 11/2002 | Mault |
| 6,175,752 | B1 | 1/2001 | Say et al. | 6,482,176 B1 | 11/2002 | Wich |
| 6,180,416 | B1 | 1/2001 | Kurnik et al. | 6,484,045 B1 | 11/2002 | Holker et al. |
| 6,185,452 | B1 | 2/2001 | Schulman et al. | 6,484,046 B1 | 11/2002 | Say et al. |
| 6,186,982 | B1 | 2/2001 | Gross et al. | 6,485,138 B1 | 11/2002 | Kubota et al. |
| 6,201,980 | B1 | 3/2001 | Darrow et al. | 6,485,461 B1 | 11/2002 | Mason et al. |
| 6,203,288 | B1 | 3/2001 | Kottke | 6,485,465 B2 | 11/2002 | Moberg et al. |
| 6,206,841 | B1 | 3/2001 | Cunningham et al. | 6,492,180 B2 | 12/2002 | Brown et al. |
| 6,208,894 | B1 | 3/2001 | Schulman et al. | 6,498,043 B1 | 12/2002 | Schulman et al. |
| 6,212,416 | B1 | 4/2001 | Ward et al. | 6,506,168 B1 | 1/2003 | Fathallah et al. |
| 6,215,206 | B1 | 4/2001 | Chitayat | 6,513,532 B2 | 2/2003 | Mault et al. |
| 6,222,514 | B1 | 4/2001 | DeLuca | 6,514,460 B1 | 2/2003 | Fendrock |
| 6,228,100 | B1 | 5/2001 | Schraga | 6,514,689 B2 | 2/2003 | Han et al. |

| Patent No. | Date | Inventor(s) |
|---|---|---|
| 6,514,718 B2 | 2/2003 | Heller et al. |
| 6,522,530 B2 | 2/2003 | Bang |
| 6,525,330 B2 | 2/2003 | Paolini et al. |
| 6,526,298 B1 | 2/2003 | Khalil et al. |
| 6,529,772 B2 | 3/2003 | Carlson et al. |
| 6,530,915 B1 | 3/2003 | Eppstein et al. |
| 6,535,753 B1 | 3/2003 | Raskas |
| 6,537,243 B1 | 3/2003 | Henning et al. |
| 6,540,675 B2 | 4/2003 | Aceti et al. |
| 6,540,891 B1 | 4/2003 | Stewart et al. |
| 6,543,224 B1 | 4/2003 | Barooah |
| 6,544,212 B2 | 4/2003 | Galley et al. |
| 6,546,269 B1 | 4/2003 | Kurnik |
| 6,549,796 B2 | 4/2003 | Sohrab |
| 6,551,276 B1 | 4/2003 | Mann et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,564,807 B1 | 5/2003 | Schulman et al. |
| 6,565,509 B1 | 5/2003 | Plante et al. |
| 6,565,738 B1 | 5/2003 | Henning et al. |
| 6,569,157 B1 | 5/2003 | Shain et al. |
| 6,571,128 B2 | 5/2003 | Lebel et al. |
| 6,571,200 B1 | 5/2003 | Mault |
| 6,576,117 B1 | 6/2003 | Iketaki et al. |
| 6,577,899 B2 | 6/2003 | Lebel et al. |
| 6,579,498 B1 | 6/2003 | Eglise |
| 6,579,690 B1 | 6/2003 | Bonnacaze et al. |
| 6,582,393 B2 | 6/2003 | Sage, Jr. |
| 6,585,644 B2 | 7/2003 | Lebel et al. |
| 6,586,971 B1 | 7/2003 | Naffziger et al. |
| 6,587,705 B1 | 7/2003 | Kim et al. |
| 6,589,229 B1 | 7/2003 | Connelly et al. |
| 6,594,514 B2 | 7/2003 | Berner et al. |
| 6,595,919 B2 | 7/2003 | Berner et al. |
| 6,596,016 B1 | 7/2003 | Vreman et al. |
| 6,600,997 B2 | 7/2003 | Deweese et al. |
| 6,602,469 B1 | 8/2003 | Maus et al. |
| 6,607,509 B2 | 8/2003 | Bobroff et al. |
| 6,610,012 B2 | 8/2003 | Mault |
| 6,612,306 B1 | 9/2003 | Mault |
| 6,615,061 B1 | 9/2003 | Khalil et al. |
| 6,615,074 B2 | 9/2003 | Mickle et al. |
| 6,618,603 B2 | 9/2003 | Varalli et al. |
| 6,620,106 B2 | 9/2003 | Mault |
| 6,623,501 B2 | 9/2003 | Heller et al. |
| 6,629,934 B2 | 10/2003 | Mault et al. |
| 6,633,095 B1 | 10/2003 | Swope et al. |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,645,142 B2 | 11/2003 | Braig et al. |
| 6,648,821 B2 | 11/2003 | Lebel et al. |
| 6,650,064 B2 | 11/2003 | Guthrie et al. |
| 6,653,091 B1 | 11/2003 | Dunn et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,980 B2 | 12/2003 | Moberg et al. |
| 6,668,196 B1 | 12/2003 | Villegas et al. |
| 6,669,663 B1 | 12/2003 | Thompson |
| 6,669,669 B2 | 12/2003 | Flaherty et al. |
| 6,670,806 B2 | 12/2003 | Wendt et al. |
| 6,679,841 B2 | 1/2004 | Bojan et al. |
| 6,687,522 B2 | 2/2004 | Tamada |
| 6,687,546 B2 | 2/2004 | Lebel et al. |
| 6,692,457 B2 | 2/2004 | Flaherty |
| 6,694,191 B2 | 2/2004 | Starkweather et al. |
| 6,695,885 B2 | 2/2004 | Schulman et al. |
| 6,699,218 B2 | 3/2004 | Flaherty et al. |
| 6,702,857 B2 | 3/2004 | Brauker et al. |
| 6,723,072 B2 | 4/2004 | Flaherty et al. |
| 6,728,560 B2 | 4/2004 | Kollias et al. |
| 6,730,200 B1 | 5/2004 | Stewart et al. |
| 6,731,976 B2 | 5/2004 | Penn et al. |
| 6,733,446 B2 | 5/2004 | Lebel et al. |
| 6,736,777 B2 | 5/2004 | Kim et al. |
| 6,736,797 B1 | 5/2004 | Larsen et al. |
| 6,738,654 B2 | 5/2004 | Sohrab |
| 6,740,059 B2 | 5/2004 | Flaherty |
| 6,740,075 B2 | 5/2004 | Lebel et al. |
| 6,741,877 B1 | 5/2004 | Shults et al. |
| 6,743,635 B2 | 6/2004 | Neel et al. |
| 6,746,582 B2 | 6/2004 | Heller et al. |
| 6,749,587 B2 | 6/2004 | Flaherty |
| 6,752,785 B2 | 6/2004 | Van Antwerp et al. |
| 6,752,787 B1 | 6/2004 | Causey, III et al. |
| 6,758,810 B2 | 7/2004 | Lebel et al. |
| 6,764,581 B1 | 7/2004 | Forrow et al. |
| 6,768,425 B2 | 7/2004 | Flaherty et al. |
| 6,770,030 B1 | 8/2004 | Schaupp et al. |
| 6,770,729 B2 | 8/2004 | Van Antwerp |
| 6,773,563 B2 | 8/2004 | Matsumoto |
| 6,779,984 B2 | 8/2004 | Lilie et al. |
| 6,789,195 B1 | 9/2004 | Prihoda et al. |
| 6,790,178 B1 | 9/2004 | Mault et al. |
| 6,794,195 B2 | 9/2004 | Colvin, Jr. |
| 6,799,861 B2 | 10/2004 | Naghi et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,816,742 B2 | 11/2004 | Kim et al. |
| 6,818,348 B1 | 11/2004 | Venkatesan et al. |
| 6,830,558 B2 | 12/2004 | Flaherty et al. |
| 6,832,114 B1 | 12/2004 | Whitehurst et al. |
| 6,833,540 B2 | 12/2004 | MacKenzie et al. |
| 6,835,553 B2 | 12/2004 | Han et al. |
| 6,837,858 B2 | 1/2005 | Cunningham et al. |
| 6,839,596 B2 | 1/2005 | Nelson et al. |
| 6,840,912 B2 | 1/2005 | Kloepfer et al. |
| 6,849,237 B2 | 2/2005 | Housefield et al. |
| 6,850,790 B2 | 2/2005 | Berner et al. |
| 6,859,831 B1 | 2/2005 | Gelvin et al. |
| 6,862,465 B2 | 3/2005 | Shults et al. |
| 6,872,200 B2 | 3/2005 | Mann et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,893,396 B2 | 5/2005 | Schulze et al. |
| 6,895,265 B2 | 5/2005 | Silver |
| 6,898,451 B2 | 5/2005 | Wuori |
| 6,899,683 B2 | 5/2005 | Mault et al. |
| 6,899,684 B2 | 5/2005 | Mault et al. |
| 6,904,301 B2 | 6/2005 | Raskas |
| 6,907,127 B1 | 6/2005 | Kravitz et al. |
| 6,908,535 B2 | 6/2005 | Rankin et al. |
| 6,916,159 B2 | 7/2005 | Rush et al. |
| 6,918,874 B1 | 7/2005 | Hatch et al. |
| 6,922,576 B2 | 7/2005 | Raskas |
| 6,922,578 B2 | 7/2005 | Eppstein et al. |
| 6,923,764 B2 | 8/2005 | Aceti et al. |
| 6,927,749 B1 | 8/2005 | Klemm |
| 6,931,327 B2 | 8/2005 | Goode, Jr. et al. |
| 6,936,029 B2 | 8/2005 | Mann et al. |
| 6,949,816 B2 | 9/2005 | Brown et al. |
| 6,950,708 B2 | 9/2005 | Bowman, IV et al. |
| 6,952,603 B2 | 10/2005 | Gerber et al. |
| 6,955,650 B2 | 10/2005 | Mault et al. |
| 6,958,129 B2 | 10/2005 | Galen et al. |
| 6,958,705 B2 | 10/2005 | Lebel et al. |
| 6,960,192 B1 | 11/2005 | Flaherty et al. |
| 6,961,448 B2 | 11/2005 | Nichols et al. |
| 6,974,437 B2 | 12/2005 | Lebel et al. |
| 6,979,326 B2 | 12/2005 | Mann et al. |
| 6,990,366 B2 | 1/2006 | Say et al. |
| 6,990,372 B2 | 1/2006 | Perron et al. |
| 6,997,911 B2 | 2/2006 | Klitmose |
| 6,997,920 B2 | 2/2006 | Mann et al. |
| 6,999,810 B2 | 2/2006 | Berner et al. |
| 7,003,340 B2 | 2/2006 | Say et al. |
| 7,003,341 B2 | 2/2006 | Say et al. |

| Patent No. | Date | Inventors |
|---|---|---|
| 7,005,857 B2 | 2/2006 | Stiene et al. |
| 7,006,858 B2 | 2/2006 | Silver et al. |
| 7,010,356 B2 | 3/2006 | Jog et al. |
| 7,011,630 B2 | 3/2006 | Desai et al. |
| 7,018,360 B2 | 3/2006 | Flaherty et al. |
| 7,020,508 B2 | 3/2006 | Stivoric et al. |
| 7,024,245 B2 | 4/2006 | Lebel et al. |
| 7,024,249 B2 | 4/2006 | Weisner et al. |
| 7,025,743 B2 | 4/2006 | Mann et al. |
| 7,029,444 B2 | 4/2006 | Shin et al. |
| 7,029,455 B2 | 4/2006 | Flaherty |
| 7,034,677 B2 | 4/2006 | Steinthal et al. |
| 7,041,468 B2 | 5/2006 | Drucker et al. |
| 7,043,287 B1 | 5/2006 | Khalil et al. |
| 7,052,251 B2 | 5/2006 | Nason et al. |
| 7,058,437 B2 | 6/2006 | Buse et al. |
| 7,067,498 B2 | 6/2006 | Wolf et al. |
| 7,070,591 B2 | 7/2006 | Adams et al. |
| 7,072,738 B2 | 7/2006 | Bonney et al. |
| 7,074,307 B2 | 7/2006 | Simpson et al. |
| 7,077,328 B2 | 7/2006 | Krishnaswamy et al. |
| 7,079,901 B1 | 7/2006 | Loftin et al. |
| 7,081,195 B2 | 7/2006 | Simpson et al. |
| 7,083,593 B2 | 8/2006 | Stultz |
| 7,086,277 B2 | 8/2006 | Tess et al. |
| 7,092,762 B1 | 8/2006 | Loftin et al. |
| 7,097,983 B2 | 8/2006 | Markovsky et al. |
| 7,098,803 B2 | 8/2006 | Mann et al. |
| 7,108,711 B2 | 9/2006 | Vogel et al. |
| 7,108,778 B2 | 9/2006 | Simpson et al. |
| 7,110,803 B2 | 9/2006 | Shults et al. |
| 7,114,502 B2 | 10/2006 | Schulman et al. |
| 7,123,206 B2 | 10/2006 | Hess et al. |
| 7,133,710 B2 | 11/2006 | Acosta et al. |
| 7,134,999 B2 | 11/2006 | Brauker et al. |
| 7,136,689 B2 | 11/2006 | Shults et al. |
| 7,136,704 B2 | 11/2006 | Schulman |
| 7,137,964 B2 | 11/2006 | Flaherty |
| 7,144,384 B2 | 12/2006 | Gorman et al. |
| 7,149,581 B2 | 12/2006 | Goedeke |
| 7,153,212 B1 | 12/2006 | Karten et al. |
| 7,154,398 B2 | 12/2006 | Chen et al. |
| 7,163,511 B2 | 1/2007 | Conn et al. |
| 7,167,818 B2 | 1/2007 | Brown |
| 7,171,274 B2 | 1/2007 | Starkweather et al. |
| 7,181,261 B2 | 2/2007 | Silver et al. |
| 7,186,566 B2 | 3/2007 | Qian |
| 7,186,791 B2 | 3/2007 | Bruno et al. |
| 7,192,450 B2 | 3/2007 | Brauker et al. |
| 7,193,521 B2 | 3/2007 | Moberg et al. |
| 7,198,603 B2 | 4/2007 | Penner et al. |
| 7,202,734 B1 | 4/2007 | Raab |
| 7,205,409 B2 | 4/2007 | Pei et al. |
| 7,208,119 B1 | 4/2007 | Kurtock et al. |
| 7,211,048 B1 | 5/2007 | Najafi et al. |
| 7,218,017 B1 | 5/2007 | Chitayat et al. |
| 7,225,535 B2 | 6/2007 | Feldman et al. |
| 7,226,278 B2 | 6/2007 | Nason et al. |
| 7,226,442 B2 | 6/2007 | Sheppard, Jr. et al. |
| 7,226,978 B2 | 6/2007 | Tapsak et al. |
| 7,258,666 B2 | 8/2007 | Brown |
| 7,266,400 B2 | 9/2007 | Fine et al. |
| 7,267,665 B2 | 9/2007 | Steil et al. |
| 7,276,029 B2 | 10/2007 | Goode, Jr. et al. |
| 7,283,867 B2 | 10/2007 | Strother et al. |
| 7,291,497 B2 | 11/2007 | Holmes et al. |
| 7,299,080 B2 | 11/2007 | Acosta et al. |
| 7,303,549 B2 | 12/2007 | Flaherty et al. |
| 7,310,544 B2 | 12/2007 | Brister et al. |
| 7,323,091 B1 | 1/2008 | Gillette et al. |
| 7,324,949 B2 | 1/2008 | Bristol et al. |
| 7,343,188 B2 | 3/2008 | Sohrab |
| 7,364,592 B2 | 4/2008 | Carr-Brendel et al. |
| 7,366,556 B2 | 4/2008 | Brister et al. |
| 7,371,247 B2 | 5/2008 | Boecker et al. |
| 7,379,765 B2 | 5/2008 | Petisce et al. |
| 7,424,318 B2 | 9/2008 | Brister et al. |
| 7,436,511 B2 | 10/2008 | Ruchti et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,480,138 B2 | 1/2009 | Kogan et al. |
| 7,494,465 B2 | 2/2009 | Brister et al. |
| 7,497,827 B2 | 3/2009 | Brister et al. |
| 7,510,526 B2 | 3/2009 | Merry et al. |
| 7,519,408 B2 | 4/2009 | Rasdal et al. |
| 7,583,190 B2 | 9/2009 | Reggiardo et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,613,491 B2 | 11/2009 | Boock et al. |
| 7,615,007 B2 | 11/2009 | Shults et al. |
| 7,620,437 B2 | 11/2009 | Reggiardo |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,679,407 B2 | 3/2010 | Reggiardo |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,181 B2 | 6/2010 | Rush et al. |
| 7,753,873 B2 | 7/2010 | Rush |
| 7,753,874 B2 | 7/2010 | Rush et al. |
| 7,756,561 B2 | 7/2010 | Reggiardo et al. |
| 7,766,864 B2 | 8/2010 | Rush et al. |
| 7,768,408 B2 | 8/2010 | Reggiardo et al. |
| 7,778,795 B2 | 8/2010 | Fukushima et al. |
| 7,850,621 B2 | 12/2010 | Briggs et al. |
| 7,882,611 B2 | 2/2011 | Shah et al. |
| 7,884,729 B2 | 2/2011 | Reggiardo et al. |
| 7,911,010 B2 | 3/2011 | Stetter |
| 7,948,370 B2 | 5/2011 | Reggiardo et al. |
| 7,954,385 B2 | 6/2011 | Raisanen |
| 2001/0016682 A1 | 8/2001 | Berner et al. |
| 2001/0016683 A1 | 8/2001 | Darrow et al. |
| 2001/0016710 A1 | 8/2001 | Nason et al. |
| 2001/0020124 A1 | 9/2001 | Tamada |
| 2001/0023095 A1 | 9/2001 | Kopley et al. |
| 2001/0024864 A1 | 9/2001 | Kopley et al. |
| 2001/0029340 A1 | 10/2001 | Mault et al. |
| 2001/0034502 A1 | 10/2001 | Moberg et al. |
| 2001/0034617 A1 | 10/2001 | Kimata |
| 2001/0037060 A1 | 11/2001 | Thompson et al. |
| 2001/0037069 A1 | 11/2001 | Carlson et al. |
| 2001/0041830 A1 | 11/2001 | Varalli et al. |
| 2001/0044581 A1 | 11/2001 | Mault |
| 2001/0044588 A1 | 11/2001 | Mault |
| 2001/0049470 A1 | 12/2001 | Mault et al. |
| 2001/0053891 A1 | 12/2001 | Ackley |
| 2001/0056255 A1 | 12/2001 | Kost et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0010414 A1 | 1/2002 | Coston et al. |
| 2002/0019022 A1 | 2/2002 | Dunn et al. |
| 2002/0019612 A1 | 2/2002 | Watanabe et al. |
| 2002/0026937 A1 | 3/2002 | Mault |
| 2002/0027164 A1 | 3/2002 | Mault et al. |
| 2002/0028995 A1 | 3/2002 | Mault |
| 2002/0032374 A1 | 3/2002 | Holker et al. |
| 2002/0040208 A1 | 4/2002 | Flaherty et al. |
| 2002/0042090 A1 | 4/2002 | Heller et al. |
| 2002/0042561 A1 | 4/2002 | Schulman et al. |
| 2002/0045808 A1 | 4/2002 | Ford et al. |
| 2002/0047867 A1 | 4/2002 | Mault et al. |
| 2002/0053637 A1 | 5/2002 | Conn et al. |
| 2002/0062069 A1 | 5/2002 | Mault |
| 2002/0065682 A1 | 5/2002 | Goldenberg |
| 2002/0068858 A1 | 6/2002 | Braig et al. |
| 2002/0077765 A1 | 6/2002 | Mault |
| 2002/0077766 A1 | 6/2002 | Mault |
| 2002/0087056 A1 | 7/2002 | Aceti et al. |
| 2002/0091312 A1 | 7/2002 | Berner et al. |
| 2002/0091454 A1 | 7/2002 | Vasko |

| | | | | | |
|---|---|---|---|---|---|
| 2002/0103425 A1 | 8/2002 | Mault | 2004/0018486 A1 | 1/2004 | Dunn et al. |
| 2002/0107433 A1 | 8/2002 | Mault | 2004/0019321 A1 | 1/2004 | Sage et al. |
| 2002/0107476 A1 | 8/2002 | Mann et al. | 2004/0027253 A1 | 2/2004 | Marsh et al. |
| 2002/0109600 A1 | 8/2002 | Mault et al. | 2004/0030226 A1 | 2/2004 | Quy |
| 2002/0118090 A1 | 8/2002 | Park et al. | 2004/0039256 A1 | 2/2004 | Kawatahara et al. |
| 2002/0119711 A1 | 8/2002 | Van Antwerp et al. | 2004/0041749 A1 | 3/2004 | Dixon |
| 2002/0124017 A1 | 9/2002 | Mault | 2004/0045879 A1 | 3/2004 | Shults et al. |
| 2002/0133378 A1 | 9/2002 | Mault et al. | 2004/0054263 A1 | 3/2004 | Moerman et al. |
| 2002/0161286 A1 | 10/2002 | Gerber et al. | 2004/0059201 A1 | 3/2004 | Ginsberg |
| 2002/0169394 A1 | 11/2002 | Eppstein et al. | 2004/0059284 A1 | 3/2004 | Nash et al. |
| 2002/0169439 A1 | 11/2002 | Flaherty et al. | 2004/0064088 A1 | 4/2004 | Gorman et al. |
| 2002/0177764 A1 | 11/2002 | Sohrab | 2004/0064096 A1 | 4/2004 | Flaherty et al. |
| 2002/0193679 A1 | 12/2002 | Malave et al. | 2004/0064133 A1 | 4/2004 | Miller et al. |
| 2003/0009133 A1 | 1/2003 | Ramey | 2004/0072357 A1 | 4/2004 | Stiene et al. |
| 2003/0023182 A1 | 1/2003 | Mault et al. | 2004/0073095 A1 | 4/2004 | Causey, III et al. |
| 2003/0023317 A1 | 1/2003 | Brauker et al. | 2004/0085215 A1 | 5/2004 | Moberg et al. |
| 2003/0028089 A1 | 2/2003 | Galley et al. | 2004/0096959 A1 | 5/2004 | Stiene et al. |
| 2003/0028120 A1 | 2/2003 | Mault et al. | 2004/0100376 A1 | 5/2004 | Lye et al. |
| 2003/0032868 A1 | 2/2003 | Graskov et al. | 2004/0106858 A1 | 6/2004 | Say et al. |
| 2003/0032874 A1 | 2/2003 | Rhodes et al. | 2004/0106859 A1 | 6/2004 | Say et al. |
| 2003/0040683 A1 | 2/2003 | Rule et al. | 2004/0106860 A1 | 6/2004 | Say et al. |
| 2003/0050546 A1 | 3/2003 | Desai et al. | 2004/0108226 A1 | 6/2004 | Polychronakos et al. |
| 2003/0050575 A1 | 3/2003 | Diermann et al. | 2004/0115067 A1 | 6/2004 | Rush et al. |
| 2003/0055380 A1 | 3/2003 | Flaherty et al. | 2004/0116847 A1 | 6/2004 | Wall |
| 2003/0060692 A1 | 3/2003 | L. Ruchti et al. | 2004/0116866 A1 | 6/2004 | Gorman et al. |
| 2003/0060765 A1 | 3/2003 | Campbell et al. | 2004/0122353 A1 | 6/2004 | Shahmirian et al. |
| 2003/0065254 A1 | 4/2003 | Schulman et al. | 2004/0132220 A1 | 7/2004 | Fish |
| 2003/0065257 A1 | 4/2003 | Mault et al. | 2004/0133092 A1 | 7/2004 | Kain |
| 2003/0065273 A1 | 4/2003 | Mault et al. | 2004/0152622 A1 | 8/2004 | Keith et al. |
| 2003/0065274 A1 | 4/2003 | Mault et al. | 2004/0153032 A1 | 8/2004 | Garribotto et al. |
| 2003/0065275 A1 | 4/2003 | Mault et al. | 2004/0158137 A1 | 8/2004 | Eppstein et al. |
| 2003/0065308 A1 | 4/2003 | Lebel et al. | 2004/0162473 A1 | 8/2004 | Sohrab |
| 2003/0078560 A1 | 4/2003 | Miller et al. | 2004/0164961 A1 | 8/2004 | Bal et al. |
| 2003/0100040 A1 | 5/2003 | Bonnecaze et al. | 2004/0167383 A1 | 8/2004 | Kim et al. |
| 2003/0100821 A1 | 5/2003 | Heller et al. | 2004/0167464 A1 | 8/2004 | Ireland et al. |
| 2003/0105407 A1 | 6/2003 | Pearce, Jr. et al. | 2004/0167801 A1 | 8/2004 | Say et al. |
| 2003/0107487 A1 | 6/2003 | Korman et al. | 2004/0171921 A1 | 9/2004 | Say et al. |
| 2003/0108976 A1 | 6/2003 | Braig et al. | 2004/0176913 A1 | 9/2004 | Kawatahara et al. |
| 2003/0118460 A1 | 6/2003 | Lilie et al. | 2004/0186362 A1 | 9/2004 | Brauker et al. |
| 2003/0130616 A1 | 7/2003 | Steil et al. | 2004/0186365 A1 | 9/2004 | Jin et al. |
| 2003/0134347 A1 | 7/2003 | Heller et al. | 2004/0193025 A1 | 9/2004 | Steil et al. |
| 2003/0135100 A1 | 7/2003 | Kim et al. | 2004/0193090 A1 | 9/2004 | Lebel et al. |
| 2003/0135333 A1 | 7/2003 | Aceti et al. | 2004/0199059 A1 | 10/2004 | Brauker et al. |
| 2003/0153820 A1 | 8/2003 | Berner et al. | 2004/0202576 A1 | 10/2004 | Aceti et al. |
| 2003/0153821 A1 | 8/2003 | Berner et al. | 2004/0207054 A1 | 10/2004 | Brown et al. |
| 2003/0154405 A1 | 8/2003 | Harrison | 2004/0208780 A1 | 10/2004 | Faries, Jr. et al. |
| 2003/0158472 A1 | 8/2003 | Sohrab | 2004/0210184 A1 | 10/2004 | Kost et al. |
| 2003/0158707 A1 | 8/2003 | Doi | 2004/0225338 A1 | 11/2004 | Lebel et al. |
| 2003/0167035 A1 | 9/2003 | Flaherty et al. | 2004/0236200 A1 | 11/2004 | Say et al. |
| 2003/0175806 A1 | 9/2003 | Rule et al. | 2004/0248204 A1 | 12/2004 | Moerman |
| 2003/0176933 A1 | 9/2003 | Lebel et al. | 2004/0249250 A1 | 12/2004 | McGee et al. |
| 2003/0181851 A1 | 9/2003 | Mann et al. | 2004/0249253 A1 | 12/2004 | Racchini et al. |
| 2003/0181852 A1 | 9/2003 | Mann et al. | 2004/0249254 A1 | 12/2004 | Racchini et al. |
| 2003/0187338 A1 | 10/2003 | Say et al. | 2004/0249999 A1 | 12/2004 | Connolly et al. |
| 2003/0187525 A1 | 10/2003 | Mann et al. | 2004/0253736 A1 | 12/2004 | Stout et al. |
| 2003/0191376 A1 | 10/2003 | Samuels et al. | 2004/0254429 A1 | 12/2004 | Yang |
| 2003/0191431 A1 | 10/2003 | Mann et al. | 2004/0254434 A1 | 12/2004 | Goodnow et al. |
| 2003/0195403 A1 | 10/2003 | Berner et al. | 2004/0254884 A1 | 12/2004 | Haber et al. |
| 2003/0195462 A1 | 10/2003 | Mann et al. | 2004/0263354 A1 | 12/2004 | Mann et al. |
| 2003/0198558 A1 | 10/2003 | Nason et al. | 2004/0264396 A1 | 12/2004 | Ginzburg et al. |
| 2003/0199825 A1 | 10/2003 | Flaherty | 2005/0003470 A1 | 1/2005 | Nelson et al. |
| 2003/0199837 A1 | 10/2003 | Vachon | 2005/0009126 A1 | 1/2005 | Andrews et al. |
| 2003/0208110 A1 | 11/2003 | Mault et al. | 2005/0010269 A1 | 1/2005 | Lebel et al. |
| 2003/0208113 A1 | 11/2003 | Mault et al. | 2005/0016276 A1 | 1/2005 | Guan et al. |
| 2003/0208133 A1 | 11/2003 | Mault | 2005/0027179 A1 | 2/2005 | Berner et al. |
| 2003/0208154 A1 | 11/2003 | Close et al. | 2005/0027180 A1 | 2/2005 | Goode, Jr. et al. |
| 2003/0208409 A1 | 11/2003 | Mault | 2005/0027181 A1 | 2/2005 | Goode, Jr. et al. |
| 2003/0212346 A1 | 11/2003 | Yuzhakov et al. | 2005/0027462 A1 | 2/2005 | Goode, Jr. et al. |
| 2003/0212364 A1 | 11/2003 | Mann et al. | 2005/0027463 A1 | 2/2005 | Goode, Jr. et al. |
| 2003/0212379 A1 | 11/2003 | Bylund et al. | 2005/0031689 A1 | 2/2005 | Shults et al. |
| 2003/0217966 A1 | 11/2003 | Tapsak et al. | 2005/0033132 A1 | 2/2005 | Shults et al. |
| 2003/0225360 A1 | 12/2003 | Eppstein et al. | 2005/0038332 A1 | 2/2005 | Saidara et al. |
| 2003/0225361 A1 | 12/2003 | Sabra | 2005/0038680 A1 | 2/2005 | McMahon |
| 2003/0226695 A1 | 12/2003 | Mault | 2005/0043598 A1 | 2/2005 | Goode, Jr. et al. |
| 2003/0232370 A1 | 12/2003 | Trifiro | 2005/0043894 A1 | 2/2005 | Fernandez |
| 2003/0235817 A1 | 12/2003 | Bartkowiak et al. | 2005/0045476 A1 | 3/2005 | Neel et al. |
| 2004/0010207 A1 | 1/2004 | Flaherty et al. | 2005/0049473 A1 | 3/2005 | Desai et al. |
| 2004/0011671 A1 | 1/2004 | Shults et al. | 2005/0051580 A1 | 3/2005 | Ramey |
| 2004/0015131 A1 | 1/2004 | Flaherty et al. | 2005/0053365 A1 | 3/2005 | Adams et al. |

| | | | | | | |
|---|---|---|---|---|---|---|
| 2005/0054909 A1 | 3/2005 | Petisce et al. | | 2006/0036139 A1 | 2/2006 | Brister et al. |
| 2005/0059926 A1 | 3/2005 | Sage, Jr. et al. | | 2006/0036140 A1 | 2/2006 | Brister et al. |
| 2005/0065464 A1 | 3/2005 | Talbot et al. | | 2006/0036141 A1 | 2/2006 | Kamath et al. |
| 2005/0090607 A1 | 4/2005 | Tapsak et al. | | 2006/0036142 A1 | 2/2006 | Brister et al. |
| 2005/0090808 A1 | 4/2005 | Malave et al. | | 2006/0036143 A1 | 2/2006 | Brister et al. |
| 2005/0112169 A1 | 5/2005 | Brauker et al. | | 2006/0036144 A1 | 2/2006 | Brister et al. |
| 2005/0113653 A1 | 5/2005 | Fox et al. | | 2006/0036145 A1 | 2/2006 | Brister et al. |
| 2005/0113657 A1 | 5/2005 | Alarcon et al. | | 2006/0036187 A1 | 2/2006 | Vos et al. |
| 2005/0113658 A1 | 5/2005 | Jacobson et al. | | 2006/0040402 A1 | 2/2006 | Brauker et al. |
| 2005/0118726 A1 | 6/2005 | Schultz et al. | | 2006/0041229 A1 | 2/2006 | Garibotto et al. |
| 2005/0121322 A1 | 6/2005 | Say et al. | | 2006/0052679 A1 | 3/2006 | Kotulla et al. |
| 2005/0124873 A1 | 6/2005 | Shults et al. | | 2006/0058602 A1 | 3/2006 | Kwiatkowski et al. |
| 2005/0137471 A1 | 6/2005 | Haar et al. | | 2006/0058627 A1 | 3/2006 | Flaherty et al. |
| 2005/0143635 A1 | 6/2005 | Kamath et al. | | 2006/0063218 A1 | 3/2006 | Bartkowiak et al. |
| 2005/0143636 A1 | 6/2005 | Zhang et al. | | 2006/0074564 A1 | 4/2006 | Bartkowiak et al. |
| 2005/0148003 A1 | 7/2005 | Keith et al. | | 2006/0094986 A1 | 5/2006 | Neel et al. |
| 2005/0154271 A1 | 7/2005 | Rasdal et al. | | 2006/0154642 A1 | 7/2006 | Scannell |
| 2005/0161346 A1 | 7/2005 | Simpson et al. | | 2006/0161078 A1 | 7/2006 | Schraga |
| 2005/0171503 A1 | 8/2005 | Van Den Berghe et al. | | 2006/0166629 A1 | 7/2006 | Reggiardo |
| 2005/0171512 A1 | 8/2005 | Flaherty | | 2006/0173259 A1 | 8/2006 | Flaherty et al. |
| 2005/0171513 A1 | 8/2005 | Mann et al. | | 2006/0173444 A1 | 8/2006 | Choy et al. |
| 2005/0173245 A1 | 8/2005 | Feldman et al. | | 2006/0173712 A1 | 8/2006 | Joubert |
| 2005/0176136 A1 | 8/2005 | Burd et al. | | 2006/0178633 A1 | 8/2006 | Garibotto et al. |
| 2005/0177036 A1 | 8/2005 | Shults et al. | | 2006/0222566 A1 | 10/2006 | Brauker et al. |
| 2005/0181012 A1 | 8/2005 | Saint et al. | | 2006/0224141 A1 | 10/2006 | Rush et al. |
| 2005/0182306 A1 | 8/2005 | Sloan | | 2006/0240403 A1 | 10/2006 | List et al. |
| 2005/0182358 A1 | 8/2005 | Veit et al. | | 2006/0247508 A1 | 11/2006 | Fennell |
| 2005/0182366 A1 | 8/2005 | Vogt et al. | | 2006/0253085 A1 | 11/2006 | Geismar et al. |
| 2005/0182451 A1 | 8/2005 | Griffin et al. | | 2006/0253086 A1 | 11/2006 | Moberg et al. |
| 2005/0187720 A1 | 8/2005 | Goode, Jr. et al. | | 2006/0273759 A1 | 12/2006 | Reggiardo |
| 2005/0192557 A1 | 9/2005 | Brauker et al. | | 2006/0282290 A1 | 12/2006 | Flaherty et al. |
| 2005/0195930 A1 | 9/2005 | Spital et al. | | 2006/0293577 A1 | 12/2006 | Morrison et al. |
| 2005/0199494 A1 | 9/2005 | Say et al. | | 2007/0016381 A1 | 1/2007 | Kamath et al. |
| 2005/0203360 A1 | 9/2005 | Brauker et al. | | 2007/0032717 A1 | 2/2007 | Brister et al. |
| 2005/0203461 A1 | 9/2005 | Flaherty et al. | | 2007/0078323 A1 | 4/2007 | Reggiardo et al. |
| 2005/0214892 A1 | 9/2005 | Kovatchev et al. | | 2007/0078818 A1 | 4/2007 | Zvitz et al. |
| 2005/0215871 A1 | 9/2005 | Feldman et al. | | 2007/0100222 A1 | 5/2007 | Mastrototaro et al. |
| 2005/0215872 A1 | 9/2005 | Berner et al. | | 2007/0106135 A1 | 5/2007 | Sloan et al. |
| 2005/0218880 A1 | 10/2005 | Ioffe | | 2007/0118405 A1 | 5/2007 | Campbell et al. |
| 2005/0235732 A1 | 10/2005 | Rush | | 2007/0135697 A1 | 6/2007 | Reggiardo |
| 2005/0238503 A1 | 10/2005 | Rush et al. | | 2007/0163880 A1 | 7/2007 | Woo et al. |
| 2005/0238507 A1 | 10/2005 | DiIanni et al. | | 2007/0173711 A1 | 7/2007 | Shah et al. |
| 2005/0239154 A1 | 10/2005 | Feldman et al. | | 2007/0176867 A1 | 8/2007 | Reggiardo et al. |
| 2005/0239518 A1 | 10/2005 | D'Agostino et al. | | 2007/0203966 A1 | 8/2007 | Brauker et al. |
| 2005/0245795 A1 | 11/2005 | Goode, Jr. et al. | | 2007/0219480 A1 | 9/2007 | Kamen et al. |
| 2005/0245799 A1 | 11/2005 | Brauker et al. | | 2007/0219597 A1 | 9/2007 | Kamen et al. |
| 2005/0249506 A1 | 11/2005 | Fuse | | 2007/0235331 A1 | 10/2007 | Simpson et al. |
| 2005/0249606 A1 | 11/2005 | Rush | | 2008/0021666 A1 | 1/2008 | Goode, Jr. et al. |
| 2005/0251083 A1 | 11/2005 | Carr-Brendel et al. | | 2008/0033254 A1 | 2/2008 | Kamath et al. |
| 2005/0261660 A1 | 11/2005 | Choi | | 2008/0045824 A1 | 2/2008 | Tapsak et al. |
| 2005/0267550 A1 | 12/2005 | Hess et al. | | 2008/0064941 A1 | 3/2008 | Funderburk et al. |
| 2005/0267780 A1 | 12/2005 | Ray et al. | | 2008/0071156 A1 | 3/2008 | Brister et al. |
| 2005/0271546 A1 | 12/2005 | Gerber et al. | | 2008/0081977 A1 | 4/2008 | Hayter et al. |
| 2005/0271547 A1 | 12/2005 | Gerber et al. | | 2008/0083617 A1 | 4/2008 | Simpson et al. |
| 2005/0272640 A1 | 12/2005 | Doyle, III et al. | | 2008/0086042 A1 | 4/2008 | Brister et al. |
| 2005/0272985 A1 | 12/2005 | Kotulla et al. | | 2008/0086044 A1 | 4/2008 | Brister et al. |
| 2005/0277844 A1 | 12/2005 | Strother et al. | | 2008/0086273 A1 | 4/2008 | Shults et al. |
| 2005/0287620 A1 | 12/2005 | Heller et al. | | 2008/0097918 A1 | 4/2008 | Spector et al. |
| 2006/0001538 A1 | 1/2006 | Kraft et al. | | 2008/0103447 A1 | 5/2008 | Reggiardo et al. |
| 2006/0001550 A1 | 1/2006 | Mann et al. | | 2008/0108942 A1 | 5/2008 | Brister et al. |
| 2006/0001551 A1 | 1/2006 | Kraft et al. | | 2008/0119703 A1 | 5/2008 | Brister et al. |
| 2006/0003398 A1 | 1/2006 | Heller et al. | | 2008/0183061 A1 | 7/2008 | Goode et al. |
| 2006/0004271 A1 | 1/2006 | Peyser et al. | | 2008/0183399 A1 | 7/2008 | Goode et al. |
| 2006/0004603 A1 | 1/2006 | Peterka et al. | | 2008/0188731 A1 | 8/2008 | Brister et al. |
| 2006/0007017 A1 | 1/2006 | Mann et al. | | 2008/0189051 A1 | 8/2008 | Goode et al. |
| 2006/0015020 A1 | 1/2006 | Neale et al. | | 2008/0194935 A1 | 8/2008 | Brister et al. |
| 2006/0015024 A1 | 1/2006 | Brister et al. | | 2008/0194936 A1 | 8/2008 | Goode et al. |
| 2006/0016700 A1 | 1/2006 | Brister et al. | | 2008/0194937 A1 | 8/2008 | Goode et al. |
| 2006/0017923 A1 | 1/2006 | Ruchti et al. | | 2008/0194938 A1 | 8/2008 | Brister et al. |
| 2006/0019327 A1 | 1/2006 | Brister et al. | | 2008/0195049 A1 | 8/2008 | Thalmann et al. |
| 2006/0020186 A1 | 1/2006 | Brister et al. | | 2008/0195232 A1 | 8/2008 | Carr-Brendel et al. |
| 2006/0020187 A1 | 1/2006 | Brister et al. | | 2008/0195967 A1 | 8/2008 | Goode et al. |
| 2006/0020188 A1 | 1/2006 | Kamath et al. | | 2008/0197024 A1 | 8/2008 | Simpson et al. |
| 2006/0020189 A1 | 1/2006 | Brister et al. | | 2008/0200788 A1 | 8/2008 | Brister et al. |
| 2006/0020190 A1 | 1/2006 | Kamath et al. | | 2008/0200789 A1 | 8/2008 | Brister et al. |
| 2006/0020191 A1 | 1/2006 | Brister et al. | | 2008/0200791 A1 | 8/2008 | Simpson et al. |
| 2006/0020192 A1 | 1/2006 | Brister et al. | | 2008/0200838 A1 | 8/2008 | Goldberger et al. |
| 2006/0025663 A1 | 2/2006 | Talbot et al. | | 2008/0200897 A1 | 8/2008 | Hoss et al. |
| 2006/0031094 A1 | 2/2006 | Cohen et al. | | 2008/0208025 A1 | 8/2008 | Shults et al. |

| | | |
|---|---|---|
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0242961 A1 | 10/2008 | Brister et al. |
| 2008/0257063 A1 | 10/2008 | Rush et al. |
| 2008/0262469 A1 | 10/2008 | Brister et al. |
| 2008/0267787 A1 | 10/2008 | Rush et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312844 A1 | 12/2008 | Hayter et al. |
| 2009/0012379 A1 | 1/2009 | Goode et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0063196 A1 | 3/2009 | Frederickson |
| 2009/0063402 A1 | 3/2009 | Hayter |
| 2009/0068954 A1 | 3/2009 | Reggiardo et al. |
| 2009/0069750 A1 | 3/2009 | Schraga |
| 2009/0076355 A1 | 3/2009 | Reggiardo |
| 2009/0076356 A1 | 3/2009 | Simpson et al. |
| 2009/0076358 A1 | 3/2009 | Reggiardo et al. |
| 2009/0076360 A1 | 3/2009 | Brister et al. |
| 2009/0076361 A1 | 3/2009 | Kamath et al. |
| 2009/0083003 A1 | 3/2009 | Reggiardo et al. |
| 2009/0099436 A1 | 4/2009 | Brister et al. |
| 2009/0105636 A1 | 4/2009 | Hayter et al. |
| 2009/0105647 A1 | 4/2009 | Rush et al. |
| 2009/0105648 A1 | 4/2009 | Rush et al. |
| 2009/0105649 A1 | 4/2009 | Rush et al. |
| 2009/0112156 A1 | 4/2009 | Rush et al. |
| 2009/0112165 A1 | 4/2009 | Rush et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163869 A1 | 6/2009 | Rush et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0216553 A1 | 8/2009 | Cellura |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0259118 A1 | 10/2009 | Feldman et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0008794 A1 | 1/2010 | Rush et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0019721 A1 | 1/2010 | Reggiardo |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0049130 A1 | 2/2010 | Rush et al. |
| 2010/0049131 A1 | 2/2010 | Rush et al. |
| 2010/0049132 A1 | 2/2010 | Rush et al. |
| 2010/0049133 A1 | 2/2010 | Rush et al. |
| 2010/0057007 A1 | 3/2010 | Rush et al. |
| 2010/0057038 A1 | 3/2010 | Rush et al. |
| 2010/0063373 A1 | 3/2010 | Kamath et al. |
| 2010/0063446 A1 | 3/2010 | Rush et al. |
| 2010/0063449 A1 | 3/2010 | Rush et al. |
| 2010/0068072 A1 | 3/2010 | Rush et al. |
| 2010/0076283 A1 | 3/2010 | Simpson et al. |
| 2010/0076371 A1 | 3/2010 | Rush et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0100041 A1 | 4/2010 | Rush et al. |
| 2010/0100042 A1 | 4/2010 | Rush et al. |
| 2010/0114028 A1 | 5/2010 | Rush et al. |
| 2010/0114029 A1 | 5/2010 | Rush et al. |
| 2010/0114073 A1 | 5/2010 | Rush et al. |
| 2010/0119693 A1 | 5/2010 | Tapsak et al. |
| 2010/0121169 A1 | 5/2010 | Petisce et al. |
| 2010/0241076 A1 | 9/2010 | Rush et al. |
| 2010/0241447 A1 | 9/2010 | Siniaguine et al. |

FOREIGN PATENT DOCUMENTS

| | | |
|---|---|---|
| EP | 0465708 | 1/1992 |
| EP | 0518524 | 12/1992 |
| EP | 0709573 | 5/1996 |
| EP | 0878707 | 11/1998 |
| EP | 0543916 | 7/2001 |
| EP | 1130638 | 9/2001 |
| EP | 0980688 | 12/2002 |
| EP | 1755443 | 11/2005 |
| EP | 1783536 | 5/2007 |
| FR | 2718492 | 10/1995 |
| JP | 1-080775 | 3/1989 |
| JP | 2001-177423 | 6/2001 |
| JP | 2001-056673 | 11/2001 |
| WO | WO-96/34637 | 11/1996 |
| WO | WO-99/56613 | 11/1999 |
| WO | WO-00/74753 | 12/2000 |
| WO | WO-01/41849 | 6/2001 |

| | | |
|---|---|---|
| WO | WO-01/54753 | 8/2001 |
| WO | WO-02/39086 | 5/2002 |
| WO | WO-02/057627 | 7/2002 |
| WO | WO-02/058537 | 8/2002 |
| WO | WO-02/084860 | 10/2002 |
| WO | WO-02/100469 | 12/2002 |
| WO | WO-03/090509 | 4/2003 |
| WO | WO-03/053503 | 7/2003 |
| WO | WO-03/071930 | 9/2003 |
| WO | WO-03/103763 | 12/2003 |
| WO | WO-2004/028337 | 4/2004 |
| WO | WO-2004/032994 | 4/2004 |
| WO | WO-2004/061420 | 7/2004 |
| WO | WO-2005/089103 | 9/2005 |
| WO | WO-2005/101994 | 11/2005 |
| WO | WO-2006/003919 | 1/2006 |
| WO | WO-2006/079114 | 7/2006 |
| WO | WO-2006/086701 | 8/2006 |
| WO | WO-2006/102412 | 9/2006 |
| WO | WO-2006/110913 | 10/2006 |
| WO | WO-2006/113408 | 10/2006 |
| WO | WO-2006/113521 | 10/2006 |
| WO | WO-2006/118947 | 11/2006 |
| WO | WO-2006/132884 | 12/2006 |
| WO | WO-2007/041072 | 4/2007 |
| WO | WO-2007/090037 | 8/2007 |
| WO | WO-2008/086541 | 7/2008 |
| WO | WO-2008/110267 | 9/2008 |

OTHER PUBLICATIONS

Barbosa, R. M., et al., "Electrochemical Studies of Zinc in Zinc-Insulin Solution", *Journal of the Royal Society of Chemistry, Analyst*, vol. 121, No. 12, 1996, pp. 1789-1793.
Bard, A. J., et al., "Methods Involving Forced Convection—Hydrodynamic Methods", *Electrochemical Methods—Fundamentals and Applications*, 2001, pp. 331-367.
Kissinger, P. T., "Introduction to Analog Instrumentation", *Laboratory Techniques in Electroanalytical Chemistry, Second Edition, Revised and Expanded*, 1996, pp. 165-194.
Ursino, M, et al., "A Mathematical Model of Cerebral Blood Flow Chemical Regulation—Part I: Diffusion Processes", *IEEE Transactions on Biomedical Engineering*, vol. 36, No. 2, 1989, pp. 183-191.
Canadian Patent Application No. 2,604,358, Examiner's Report mailed Feb. 9, 2010.
Canadian Patent Application No. 2,604,358, Examiner's Report mailed Jun. 30, 2009.
Canadian Patent Application No. 2,604,498, Examiner's Report mailed Jul. 16, 2009.
Canadian Patent Application No. 2,604,695, Examiner's Report mailed Apr. 9, 2010.
Chinese Patent Application No. 200680018051.0, Original Language and English Translation of First Office Action mailed Apr. 20, 2009.
Chinese Patent Application No. 200680018073.7, Original Language and English Translation of First Office Action mailed Jan. 23, 2009.
European Patent Application No. 03770727.0, Supplementary European Search Report mailed Jun. 12, 2008.
European Patent Application No. 06750300.3, Extended European Search Report mailed Aug. 20, 2009.
PCT Application No. PCT/US2003/032191, International Preliminary Examination Report mailed Jan. 4, 2005.
PCT Application No. PCT/US2003/032191, International Search Report and Written Opinion of the International Searching Authority mailed Apr. 1, 2004.
PCT Application No. PCT/US2006/014022, International Preliminary Report on Patentability and Written Opinion of the International Searching Authority mailed Oct. 25, 2007.
PCT Application No. PCT/US2006/014022, International Search Report and Written Opinion of the International Searching Authority mailed May 23, 2007.
PCT Application No. PCT/US2006/014228, International Preliminary Report on Patentability and Written Opinion of the International Searching Authority mailed Oct. 25, 2007.
PCT Application No. PCT/US2006/014228, International Search Report and Written Opinion of the International Searching Authority mailed May 26, 2007.
PCT Application No. PCT/US2006/014281, International Preliminary Report on Patentability and Written Opinion of the International Searching Authority mailed Oct. 25, 2007.
PCT Application No. PCT/US2006/014281, International Search Report and Written Opinion of the International Searching Authority mailed Feb. 22, 2007.
U.S. Appl. No. 11/106,155, Office Action mailed Aug. 13, 2009.
U.S. Appl. No. 11/106,155, Office Action mailed Jan. 14, 2010.
U.S. Appl. No. 11/106,155, Office Action mailed May 19, 2010.
U.S. Appl. No. 11/106,155, Office Action mailed Oct. 29, 2008.
U.S. Appl. No. 11/106,256, Notice of Allowance mailed Apr. 18, 2008.
U.S. Appl. No. 11/106,256, Office Action mailed Jan. 24, 2008.
U.S. Appl. No. 11/106,256, Office Action mailed May 3, 2007.
U.S. Appl. No. 12/345,545, Office Action mailed May 4, 2010.
U.S. Appl. No. 12/345,545, Office Action mailed Oct. 13, 2009.
U.S. Appl. No. 12/345,554, Office Action mailed May 4, 2010.
U.S. Appl. No. 12/345,554, Office Action mailed Oct. 13, 2009.
U.S. Appl. No. 12/345,563, Office Action mailed Jun. 1, 2010.
U.S. Appl. No. 12/345,571, Office Action mailed Jun. 29, 2010.
U.S. Appl. No. 12/345,586, Office Action mailed Jul. 27, 2010.
U.S. Appl. No. 12/345,591, Office Action mailed Jul. 27, 2010.
U.S. Appl. No. 12/345,595, Notice of Allowance mailed May 6, 2010.
U.S. Appl. No. 12/345,595, Office Action mailed Jan. 12, 2010.
U.S. Appl. No. 12/345,597, Notice of Allowance mailed May 14, 2010.
U.S. Appl. No. 12/345,597, Office Action mailed Jan. 11, 2010.
U.S. Appl. No. 12/345,603, Notice of Allowance mailed May 13, 2010.
U.S. Appl. No. 12/345,603, Office Action mailed Dec. 31, 2009.
Abstract of Japanese Publication No. JP-2001-077423, Published Mar. 23, 2001.
Canadian Patent Application No. 2,604,695, Notice of Allowance mailed Nov. 22, 2010.
U.S. Appl. No. 11/105,711, Advisory Action mailed Apr. 2, 2009.
U.S. Appl. No. 11/105,711, Notice of Allowance mailed Apr. 12, 2010.
U.S. Appl. No. 11/105,711, Office Action mailed Jun. 2, 2009.
U.S. Appl. No. 11/105,711, Office Action mailed Mar. 21, 2008.
U.S. Appl. No. 11/105,711, Office Action mailed Oct. 17, 2008.
U.S. Appl. No. 11/105,711, Office Action mailed Oct. 30, 2009.
U.S. Appl. No. 11/106,155, Advisory Action mailed Nov. 1, 2010.
U.S. Appl. No. 11/106,155, Office Action mailed Jan. 5, 2011.
U.S. Appl. No. 11/106,155, Office Action mailed Sep. 27, 2010.
U.S. Appl. No. 12/345,545, Advisory Action mailed Jul. 7, 2010.
U.S. Appl. No. 12/345,545, Office Action mailed Nov. 19, 2010.
U.S. Appl. No. 12/345,554, Advisory Action mailed Jul. 13, 2010.
U.S. Appl. No. 12/345,554, Office Action mailed Nov. 22, 2010.
U.S. Appl. No. 12/345,563, Office Action mailed Sep. 28, 2010.
U.S. Appl. No. 12/345,571, Notice of Allowance Dec. 7, 2010.
U.S. Appl. No. 12/345,586, Office Action mailed Dec. 27, 2010.
U.S. Appl. No. 12/345,591, Office Action mailed Jan. 6, 2011.
U.S. Appl. No. 12/562,296, Office Action mailed Oct. 21, 2010.
U.S. Appl. No. 12/563,502, Notice of Allowance mailed Feb. 23, 2011.
U.S. Appl. No. 12/563,502, Office Action mailed Aug. 4, 2010.
U.S. Appl. No. 12/563,502, Office Action mailed Jan. 5, 2011.
U.S. Appl. No. 12/565,130, Notice of Allowance mailed Mar. 2, 2011.
U.S. Appl. No. 12/565,130, Office Action mailed Aug. 4, 2010.
U.S. Appl. No. 12/565,130, Office Action mailed Jan. 5, 2011.
U.S. Appl. No. 12/565,146, Office Action mailed Nov. 29, 2010.
European Patent Application No. 10013445.1 European Search Report mailed Apr. 14, 2011.
European Patent Application No. 10013449.3 European Search Report mailed Jan. 31, 2011.
U.S. Appl. No. 12/345,563, Office Action mailed Apr. 8, 2011.
European Patent Application No. 06750136.1, Extended European Search Report mailed Sep. 9, 2011.

Canadian Patent Application No. 2,501,825, Notice of Allowance mailed Jan. 27, 2009.
Canadian Patent Application No. 2,604,358, Notice of Allowance mailed Oct. 5, 2010.
Canadian Patent Application No. 2,604,498, Notice of Allowance mailed Mar. 1, 2010.
Chinese Patent Application No. 200680018051.0, English Translation & Original Language of Office of Office Action mailed Feb. 21, 2012.
Chinese Patent Application No. 200680018073.7, English Translation of Office Action mailed Aug. 7, 2009.
U.S. Appl. No. 12/562,296, Advisory Action mailed Jan. 26, 2011.
U.S. Appl. No. 12/562,296, Office Action mailed Dec. 21, 2011.
U.S. Appl. No. 12/563,479, Notice of Allowance Sep. 20, 2011.
U.S. Appl. No. 12/563,479, Office Action mailed Jun. 9, 2011.
U.S. Appl. No. 12/563,798, Office Action mailed Dec. 20, 2011.
U.S. Appl. No. 12/563,798, Office Action mailed Jul. 20, 2011.
U.S. Appl. No. 12/563,798, Office Action mailed Mar. 4, 2011.
U.S. Appl. No. 12/565,119, Notice of Allowance mailed Oct. 28, 2011.
U.S. Appl. No. 12/565,119, Office Action mailed Jul. 15, 2011.
U.S. Appl. No. 12/565,146, Office Action mailed Apr. 27, 2011.
U.S. Appl. No. 12/565,146, Office Action mailed Jul. 20, 2011.
U.S. Appl. No. 12/572,075, Office Action mailed Feb. 21, 2012.
U.S. Appl. No. 12/572,123, Notice of Allowance mailed Nov. 8, 2011.
U.S. Appl. No. 12/572,123, Office Action mailed Jul. 15, 2011.
U.S. Appl. No. 12/572,136, Office Action mailed May 11, 2011.
U.S. Appl. No. 12/572,136, Office Action mailed Nov. 9, 2011.
U.S. Appl. No. 12/572,145, Office Action mailed Aug. 17, 2011.
U.S. Appl. No. 12/572,145, Office Action mailed Dec. 21, 2011.
U.S. Appl. No. 12/572,145, Office Action mailed Mar. 21, 2011.
U.S. Appl. No. 12/572,891, Office Action mailed May 11, 2011.
U.S. Appl. No. 12/572,891, Office Action mailed Nov. 9, 2011.
U.S. Appl. No. 12/610,864, Office Action mailed Jul. 13, 2011.
U.S. Appl. No. 12/610,890, Notice of Allowance mailed Oct. 28, 2011.
U.S. Appl. No. 12/610,890, Office Action mailed Jul. 13, 2011.
U.S. Appl. No. 12/610,932, Office Action mailed Nov. 8, 2011.
U.S. Appl. No. 12/616,037, Office Action mailed Dec. 20, 2011.
U.S. Appl. No. 12/616,037, Office Action mailed Jul. 11, 2011.
U.S. Appl. No. 12/616,037, Office Action mailed Mar. 10, 2011.
U.S. Appl. No. 12/616,045, Office Action mailed Jan. 5, 2012.
U.S. Appl. No. 12/616,045, Office Action mailed Jun. 27, 2011.
U.S. Appl. No. 13/115,100 Office Action mailed Jul. 17, 2012.
Chinese Patent Application No. 200680018072.2.0, English Translation & Original Language of Office Action mailed Aug. 2, 2010.
Chinese Patent Application No. 200680018072.2.0, English Translation & Original Language of Office Action mailed May 23, 2011.
U.S. Appl. No. 11/106,155, Notice of Allowance mailed Jun. 6, 2011.
U.S. Appl. No. 12/345,545, Notice of Allowance mailed Aug. 30, 2011.
U.S. Appl. No. 12/345,545, Office Action mailed May 9, 2011.
U.S. Appl. No. 12/345,554, Notice of Allowance mailed Jun. 10, 2011.
U.S. Appl. No. 12/345,563, Notice of Allowance mailed Jul. 25, 2011.
U.S. Appl. No. 12/345,586, Notice of Allowance mailed Jul. 29, 2011.
U.S. Appl. No. 12/345,591, Notice of Allowance mailed Aug. 10, 2011.

FLUID DELIVERY DEVICE WITH AUTOCALIBRATION

CROSS REFERENCE TO RELATED APPLICATIONS

The present application is a continuation of U.S. application Ser. No. 11/105,711 filed Apr. 13, 2005, now U.S. Pat. No. 7,727,181, which is a continuation-in-part of U.S. application Ser. No. 10/683,659 of Benjamin M. Rush et al., filed on Oct. 9, 2003, now U.S. Pat. No. 6,916,159 which is related to and claims priority based on U.S. Provisional Application No. 60/417,464, entitled "Disposable Pump for Drug Delivery System", filed on Oct. 9, 2002, and U.S. Provisional Application No. 60/424,613, entitled "Disposable Pump and Actuation Circuit for Drug Delivery System," filed on Nov. 6, 2002, each of which is hereby incorporated by this reference in its entirety. The parent application, U.S. application Ser. No. 10/683,659, was published as U.S. Patent Application Publication No. 2004/0115067 A1 and issued as U.S. Pat. No. 6,916,159 on Jul. 12, 2005. The present application is related to U.S. application Ser. No. 11/106,155 of Benjamin M. Rush et al., filed Apr. 13, 2005 entitled "Variable Volume, Shape Memory Actuated Insulin Dispensing Pump," and U.S. application Ser. No. 11/106,256 of Benjamin M. Rush, filed Apr. 13, 2005 entitled "Methods for Use in Assessing a Flow Condition of a Fluid," each of which is hereby incorporated herein, in its entirety, by this reference.

FIELD OF THE INVENTION

The present invention relates generally to fluid delivery devices such as pumps and relates more specifically to control and use of a small scale pump.

BACKGROUND OF THE INVENTION

Although the present invention may be used with many different types and sizes of pumps, the present invention is particularly useful with miniature or micro disposable pumps. One application for such a pump is in the delivery of insulin.

One type of miniature or micro pump utilizes a piston to push a volume of liquid defined by the volume (bore×stroke) of the piston and the volume of an accompanying diaphragm. A dose of the liquid, for example insulin, is said for purposes of discussion, to equal the volume of liquid expelled in one delivery stroke of the piston.

One characteristic of a miniature pump is that the piston diaphragm assembly requires extremely high manufacturing tolerances in order to generate a reproducible dose volume from one pump to the next. For example, with a typically sized miniature piston type pump the volume of the dose will vary by 0.5% per $\frac{1}{10000}$ inch of variation in the stroke length. The stroke length is determined by the linear dimensions of three separate components, the piston, the cylinder, and the diaphragm, each of which has tolerances over $\frac{1}{10000}$ inch. A coincidence of maximum variation in each of these components would result in a dose volume variation of ±15% from the nominal value. Additional tolerances associated with the diaphragm diameter and the piston head diameter further compound the problem.

Given that some applications of such a pump involve drug delivery, delivering a dose volume that is the same from pump to pump is non trivial. This is especially true in the case of disposable pumps, where a pump is regularly replaced with another pump of the same model. Regardless of the application of the pump, it is desirable to accommodate manufacturing tolerances and produce repeatable pumps with accurate dosage delivery.

SUMMARY OF INVENTION

The present invention provides a simple, inexpensive and reliable mechanism and method for determining the dose size produced by a given pump, which is then used to calibrate the pump and thereby normalize manufacturing variations in the volume of the pump. This results in more reliable and repeatable fluid delivery from one pump to the next of a given design.

Another aspect of the present invention comprises measuring the dose volume of a pump, preferably during the initial priming process, or alternatively anytime thereafter. This volume is then used to calibrate the timing of the dosing period. For example, if the actual measured volume of a particular pump is determined to be 15% larger than a basis value, such as the expected nominal value of the volume, then the timing of all subsequent delivery rates is reduced accordingly. The measurement can be made as part of the manufacturing process or can be made by the user as part of a pump initialization process. The measurement can also automatically be made by the pump at any time during operation of the pump. The calibration or adjustment of pump delivery is preferably made before usage of the pump by a user, but may be made any time during the life of the pump.

Another aspect involves a method of dispensing a liquid to a user with a portable dispensing device. The method comprises pumping the liquid, detecting arrival of the liquid at a first sensor, detecting arrival of the liquid at a second sensor, measuring the time elapsed from the arrival of the liquid at the first sensor to the arrival of the liquid at the second sensor, calculating the volumetric flow rate of the dispensing device, and adjusting the volumetric flow rate of the dispensing of the device.

Yet another aspect involves a method of administering a liquid including a drug to a user with a device worn or carried by a user. The method comprises providing a disposable component comprising a pump element, providing a durable component comprising a microprocessor, the disposable component configured to mate and operate with the durable component, initiating the flow of the liquid through a portion of the device with a known volume, the flow comprising a plurality of doses, determining the time necessary to pump the known volume, and determining the volume of a dose.

Additional aspects, advantages and features of the present invention are included in the following description of exemplary examples thereof, which description should be taken in conjunction with the accompanying figures, and wherein like (and similar) numerals are used to describe the same feature throughout the figures. All patents, patent applications, articles and other publications referenced herein are hereby incorporated herein by this reference in their entirety for all purposes.

DETAILED DESCRIPTION OF THE PREFERRED EMBODIMENTS

Figure 1A:
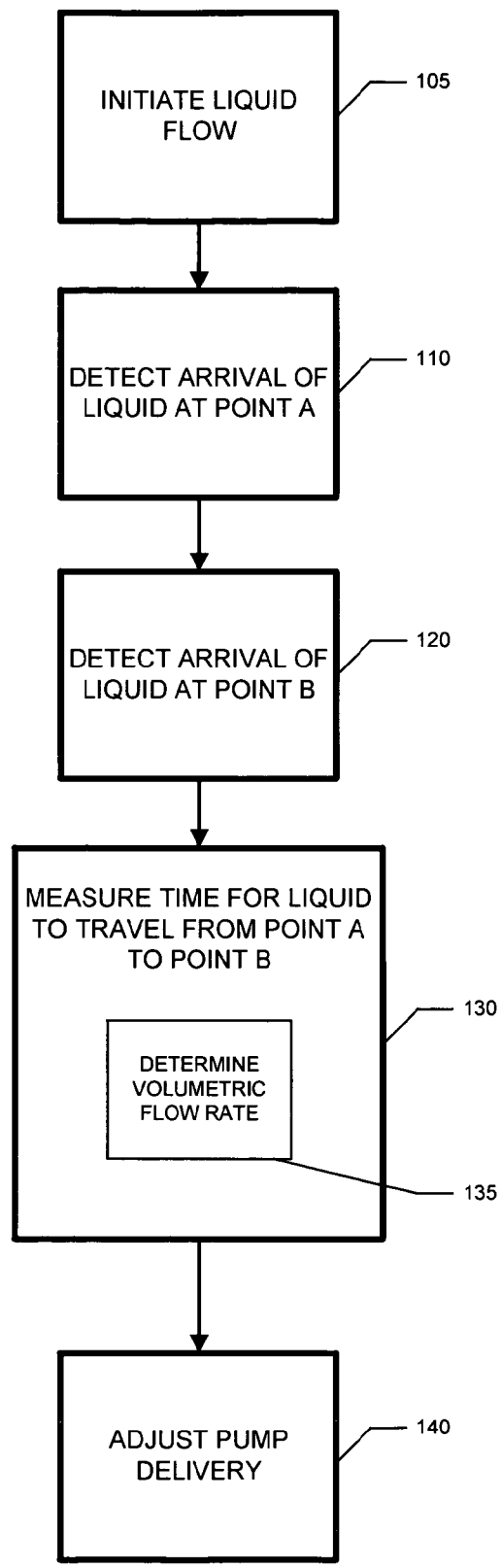
FIG. 1A is a flow chart of operation of an embodiment of the present invention.

It is important to eliminate the variations from one pump to the next (of the same design) that are a result of manufacturing limitations. The present invention can be used to minimize the effects of these variations and results in accurate delivery in any type of liquid pump.

As discussed in the background, there is one type of liquid pump with which the present invention is particularly advantageous, the miniature piston type pump. The piston diaphragm assembly of a miniature pump requires extremely high manufacturing tolerances in order to generate a reproducible dose volume from one pump to the next. Even with high precision manufacturing, a not insignificant variation from one pump to the next of a given design may be present. This is less than ideal, especially in applications of the pump involving drug delivery or other medicinal applications.

The present invention provides a simple, inexpensive and reliable mechanism and method for minimizing, or "zeroing out" the differences from pump to pump. One aspect involves a logic or processor controlled routine that may be thought of as an automatic calibration of the device. In a most general sense, this involves measuring the volume of a dosage produced by a given pump, comparing that dosage to a nominal dosage volume expected for that particular type of pump design, and then adjusting the pump output accordingly. This can also be accomplished by measuring the flow rate and then adjusting accordingly. Both volume and flow rate measurement comprise usage of one or more sensors that indicate the presence of liquid at a given point or points. Although there are many ways of adjusting the output of the pump, the preferred way of doing this is by calculating a ratio of a measured versus expected volume and calibrating the delivery based upon the ratio.

Although the present invention can be used with the delivery of any fluid in any environment, in the medical environment where the present invention is particularly suitable, the types of liquids that can be delivered include, but are not limited to: insulin, antibiotics, anesthetics, nutritional fluids, analgesics, hormones or related drugs, gene therapy drugs, anticoagulants, cardiovascular medications, HIV treatments, cancer treatments, etc. These can be delivered transcutaneously, through a type of patch on the skin, or the liquid may be evaporated and inhaled. The present invention is not limited to the delivery of these liquids or by the means of ingress into the patient's system, and these are only examples, not an exhaustive list.

Again, one application where the present invention may be particularly useful is in the delivery of insulin. Specifically, it may be useful in delivery of small quantities of insulin regularly with what is known as a miniature or micro pump. As the name implies, a miniature or micro pump delivers relatively small quantities. In the preferred embodiments described, which are tailored to insulin delivery, each actuation or dose of such a micro or miniature pump is on the order of approximately 0.5 to 5.0 microliters, with a potential total delivery of around 1000 microliters per day. Delivery volumes for other liquids (in the medical arena, that is) may be as high as around 5000 microliters or 5 cc's per day.

Figure 1B:
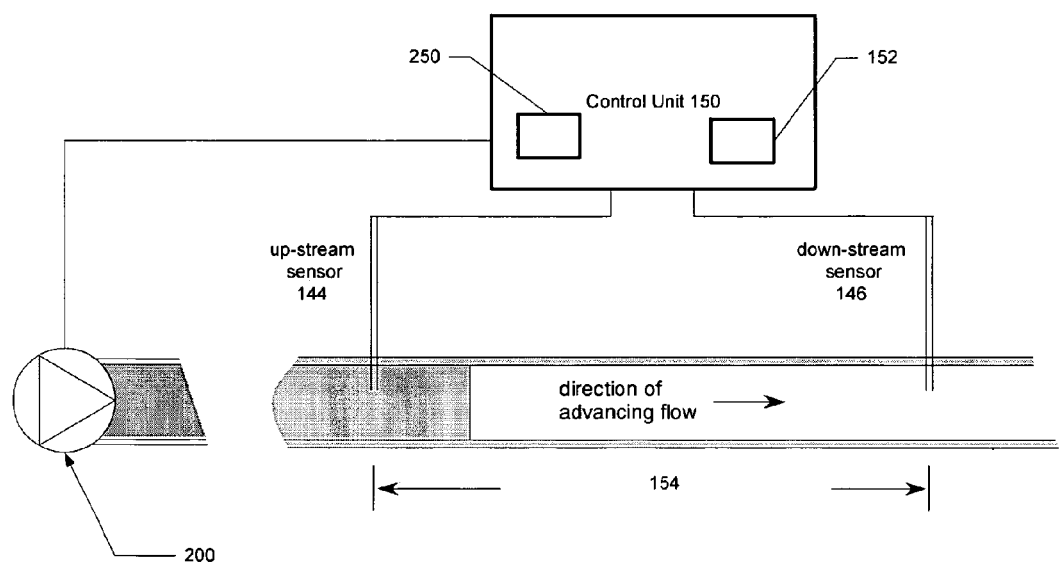
FIG. 1B is a diagram of an embodiment of the present invention referenced in FIG. 1A.

FIG. 1A is a flow chart describing operation according to an embodiment of the present invention seen in the schematic diagram of FIG. 1B. The process depicted in FIG. 1A can be performed at any time. It may also be done in conjunction with priming of the pump. In FIG. 1B there are two sensors, up-stream sensor 144, and down stream sensor 146, with a known volume between the two sensors. In this embodiment the known volume, or calibration region 154, has a cylindrical shape, but any geometric (regular or irregular) shape may be employed, so long as the volume is known or can be ascertained. The geometry of the calibration region should be such that it can be manufactured with sufficiently high reproducibility, and the volume of the calibration region is preferably much greater than the volume of an individual dose of insulin solution. This ensures good resolution and accuracy in the measurement. The sensors are connected to control unit 150, which is also connected to pump 200. Control unit 150 comprises drive circuitry 250 and logic unit 152, which is preferably in the form of a microprocessor. Each sensor comprises a pair of conductive electrodes, and when current passes between the electrodes of the pair, it indicates the presence of a liquid by the establishment of electrical continuity between the pair of electrodes. As long as the liquid has some measure of electrical conductivity, the presence of the liquid can be measured. As is appreciated in the art, the material of the electrodes may be tailored for the particular application. In the case of insulin, gold electrodes work well. As mentioned previously, pump 200 may be any type of liquid pump. In applications where cost is a driving factor, it is often preferable to utilize a pump that is driven by a shape memory actuator. This is particularly the case in the medical field, where devices are disposed of and replaced relatively frequently for various reasons.

The control unit 150 controls operation of the pump 200 and of the fluid delivery device generally, which may also comprise a user interface (not shown) for setting various operating parameters such as the delivery rate and for starting and stopping the device. The control unit also initiates and controls calibration of the device. For more information on the construction and operation of such a device, please refer to U.S. application Ser. No. 10/683,659 filed on Oct. 9, 2003, published as U.S. Patent Application Publication No. 2004/0115067 A1, and hereby incorporated by this reference in its entirety.

Returning to the flowchart of FIG. 1A, in step 105 the control unit initiates liquid flow. Then, in step 110, the control unit detects the arrival of the liquid at point A, which is a first point. This corresponds to up-stream sensor 144 in FIG. 1B. This can be done either when the liquid first advances or by placing an interruption in the flow stream before it reaches up-stream sensor 144. For instance, one way of interrupting the flow is to interject a gas bubble into the flow stream. In step 120, the control unit detects the arrival of the advancing liquid at point B, which corresponds to down-stream sensor 146 in FIG. 1B. In the case of a cylindrical calibration region 154 with a known diameter, the volume of the region is known if the distance between the two sensors is known.

In step 130, control unit 150 measures the time it takes for the liquid to travel from point A to point B. The volumetric flow rate is also calculated in step 135 based upon the time measured and the known volume between the points. This information is then used to adjust the delivery of the pump, as is seen in step 140. This process can take place at any time. It can be used initially to calibrate the pump, or during any time during operation of the device. Even if a discrete break is not inserted into the flow stream, the sensors may also indicate the flow rate of the device. The signal produced by the electrodes will increase as the rate of conduction of the liquid increases. Thus, given that the liquid is uniformly mixed, the signal will increase as the flow rate increases. For a given electrode/liquid combination, a profile of the output versus flow rate can be determined for given concentrations. The controller can then reference this data stored in memory to determine the flow rate. For more information on this, please refer to a co-pending U.S. application Ser. No. 11/106,256 of Benjamin M. Rush, entitled "Methods for Use in Assessing a Flow Condition of a Fluid," which is hereby incorporated by this reference in its entirety.

Figure 2B:
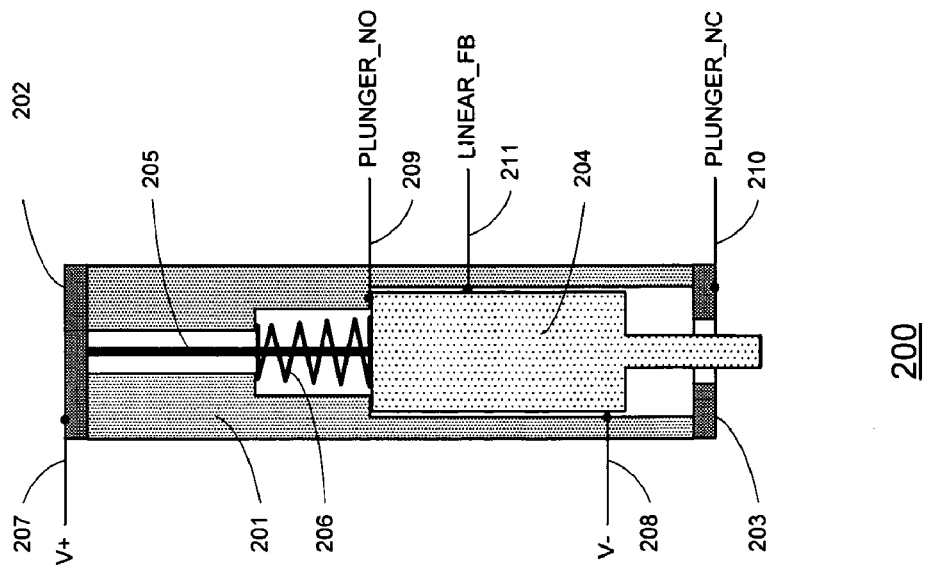
FIG. 2B illustrates pump 200, an embodiment of one type of pump that may be implemented with the present invention, shown in a second state.
Figure 2A:
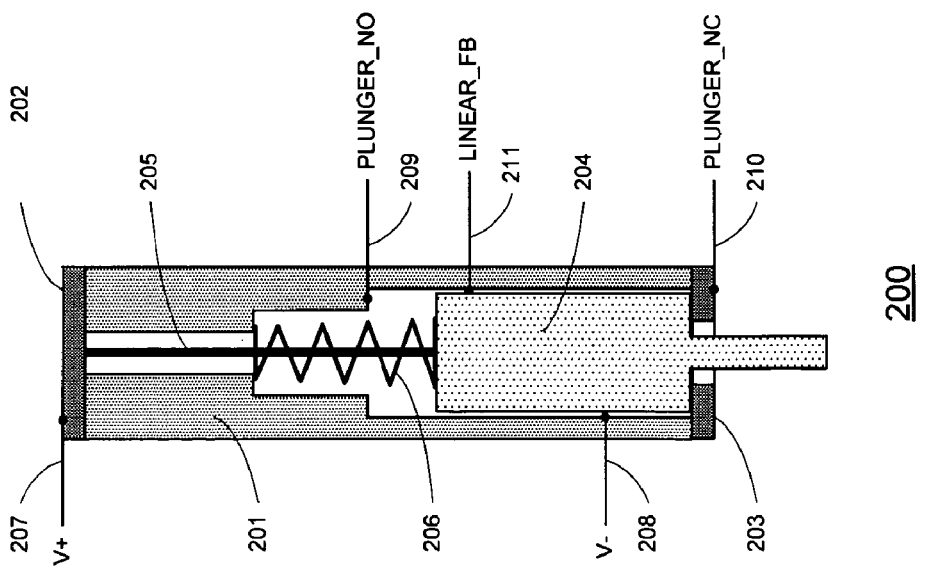
FIG. 2A illustrates pump 200, an embodiment of one type of pump that may be implemented with the present invention, shown in a first state.

FIGS. 2A and 2B illustrate pump 200, an embodiment of one type of pump particularly suited for use in the present invention. This pump is driven by a shape memory element 206 and employs feedback including that from switch 209, switch 210, and linear feedback system 211, all of which indicate the position of piston 204.

Pump 200 is shown in the inactive state in FIG. 2A, and the active state in FIG. 1B. Switch 209 indicates that the plunger or pump is in the open position, and switch 210 indicates it is in the closed position. The pump body comprises a case 201, a top cap 202, and a plunger cap 203. Within the pump is a plunger 204 that is normally (in the inactive state) held against the plunger cap 203 by a plunger bias spring 205. The plunger 204 is connected to shape memory element 206 which contracts when heated by a pulse or pulses of current flowing from the V+207 contact to the V−208 contact through the shape memory element 206 (where the V−208 contact may be the system ground reference). The power in each pulse is determined by the voltage applied to the shaped memory element through the contacts. It is worth noting that the case is made of an insulating material while the plunger is either made of a conductive material (e.g. metal) or is coated with an appropriately conductive material.

FIG. 2A depicts the pump in the inactive state where the shape memory element 206 is not contracted, and the plunger 204 is held against the plunger cap 203 by the plunger bias spring 205. This is the state to which the pump returns after each activation or pumping cycle.

FIG. 2B shows the pump in the active state where the shaped memory element 206 has contracted enough to pull the plunger 204 up against a stop built into the case 201.

Figure 2C:
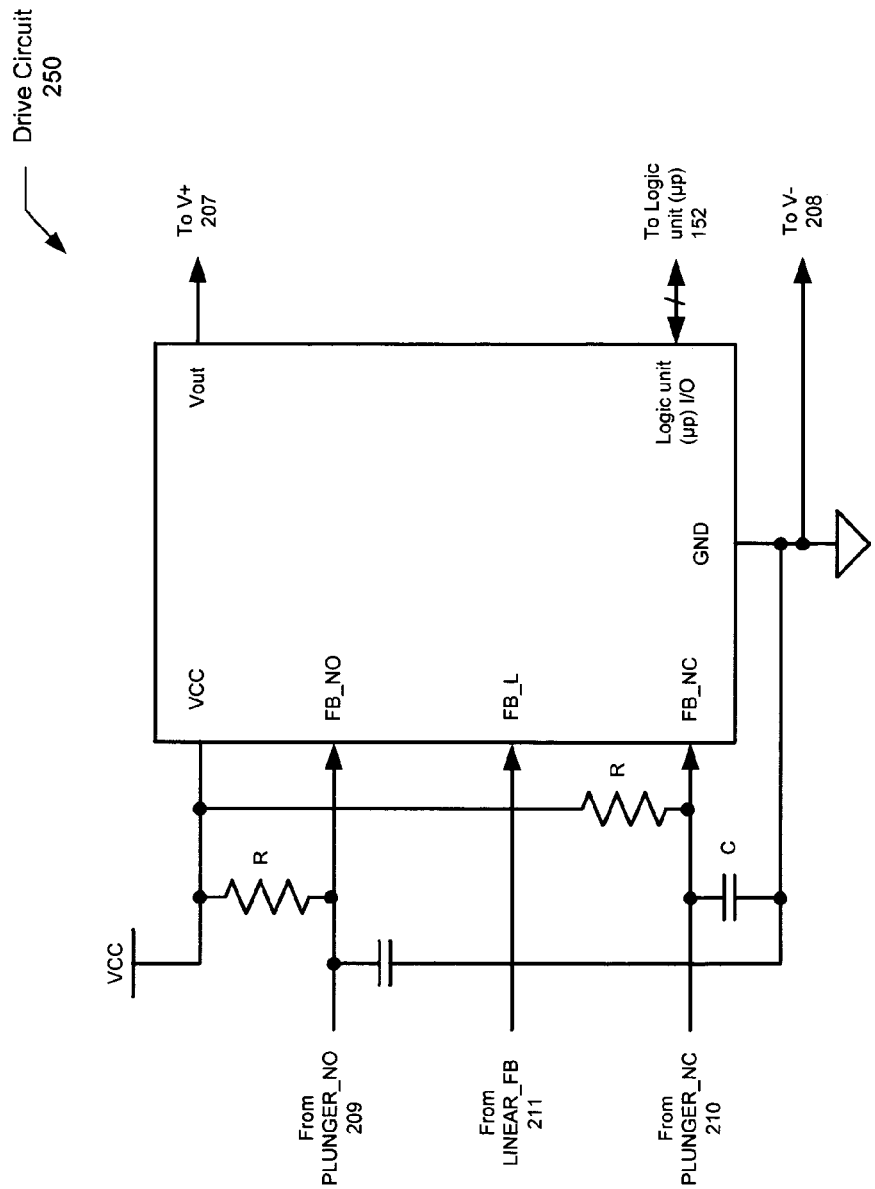
FIG. 2C is a diagram illustrating an example of a drive circuit for use with pump 200.

FIG. 2C illustrates drive circuit 250, an embodiment of a circuit that may be used with pump 200. Drive circuit 250 includes input and feedback to/from logic unit 152, which preferably comprises a microprocessor, as mentioned previously. For more information on this and other aspects of a shape memory actuated pump, please refer to co-pending U.S. application Ser. No. 11/106,155 of Benjamin M. Rush et al., entitled "Variable Volume, Shape Memory Actuated Insulin Dispensing Pump," which is hereby incorporated by this reference in its entirety.

Figures 3, 4:
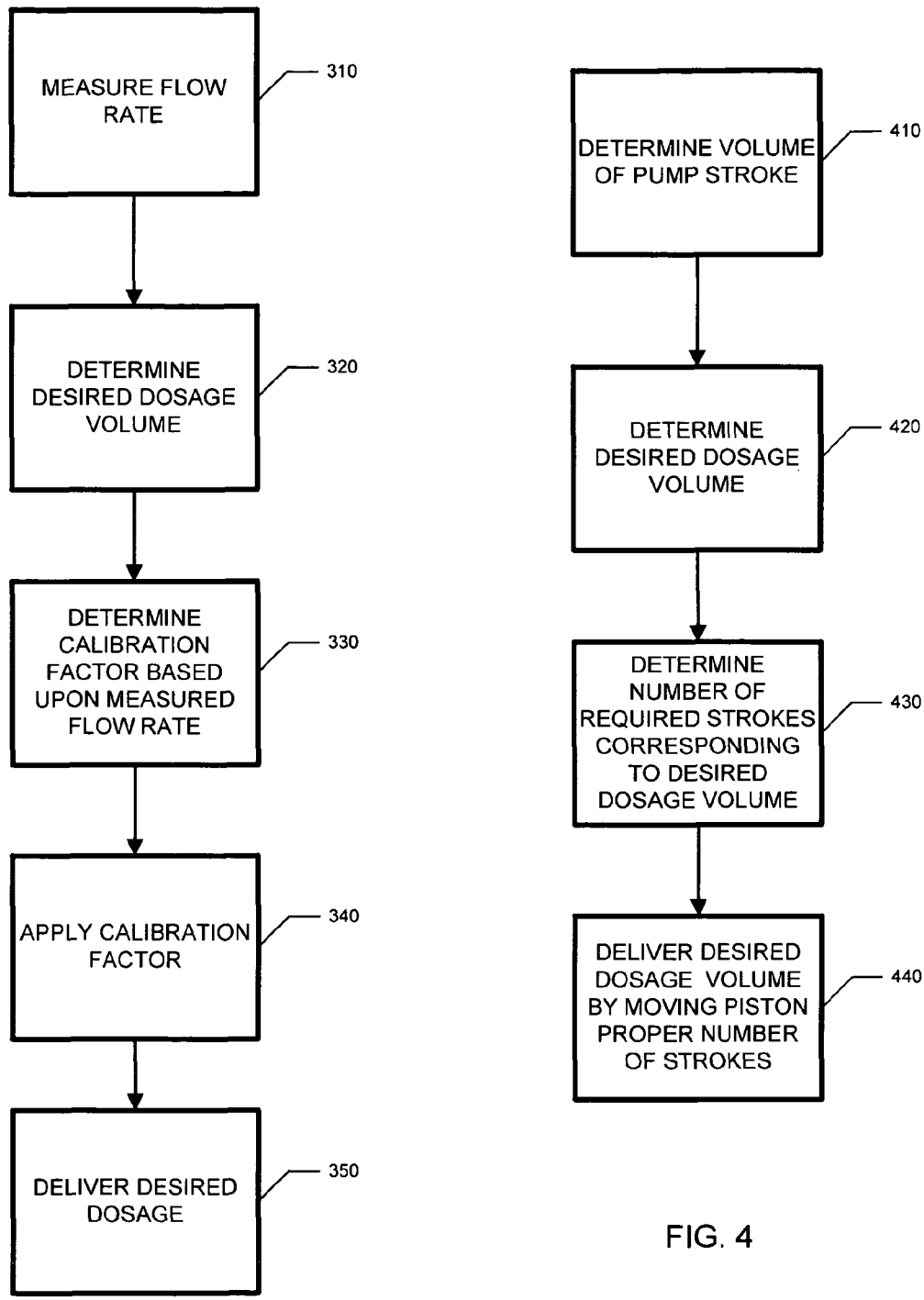
FIG. 3 is a flowchart depicting operation according to one embodiment of the present invention.
FIG. 4 is a flow chart of operation according to an embodiment of the present invention.

FIG. 3 is a flowchart depicting operation according to one embodiment of the present invention. In step 310, the control unit measures the flow rate, as discussed earlier. Next in step 320, the system determines the desired dosage volume. This may be done automatically or may be entered by the user. In step 330, the system determines the calibration factor based upon the measured flow rate. The calibration factor preferably comprises a ratio of the expected volume of a dose versus the actual volume of a dose. In the case of the piston type pump earlier described, the calibration factor comprises a ratio of the nominal volume of the cylinder versus the actual volume of the cylinder. The nominal volume is either the value of the volume expected from the design specifications or the value expected based upon the nominal value of a large sample of production pieces. Once it has been determined, the calibration factor is applied in step 340 and will be applied to subsequent operation of the system, including when a desired dosage is delivered in step 350.

FIG. 4 is a flowchart depicting operation according to another embodiment of the present invention. In step 410, the volume delivered in one pump stroke is determined. In step 420, the system determines the desired dosage volume, which may be done automatically or entered by the user. Next in step 430 the system determines the number of required strokes corresponding to a desired dosage volume. Because of the linear feedback of the present invention, the system may deliver fractions of a stroke, and the number of strokes may include any number and fraction of strokes. Next, in step 440, the system delivers the desired dosage volume by moving the piston the proper number of strokes.

Figure 5:
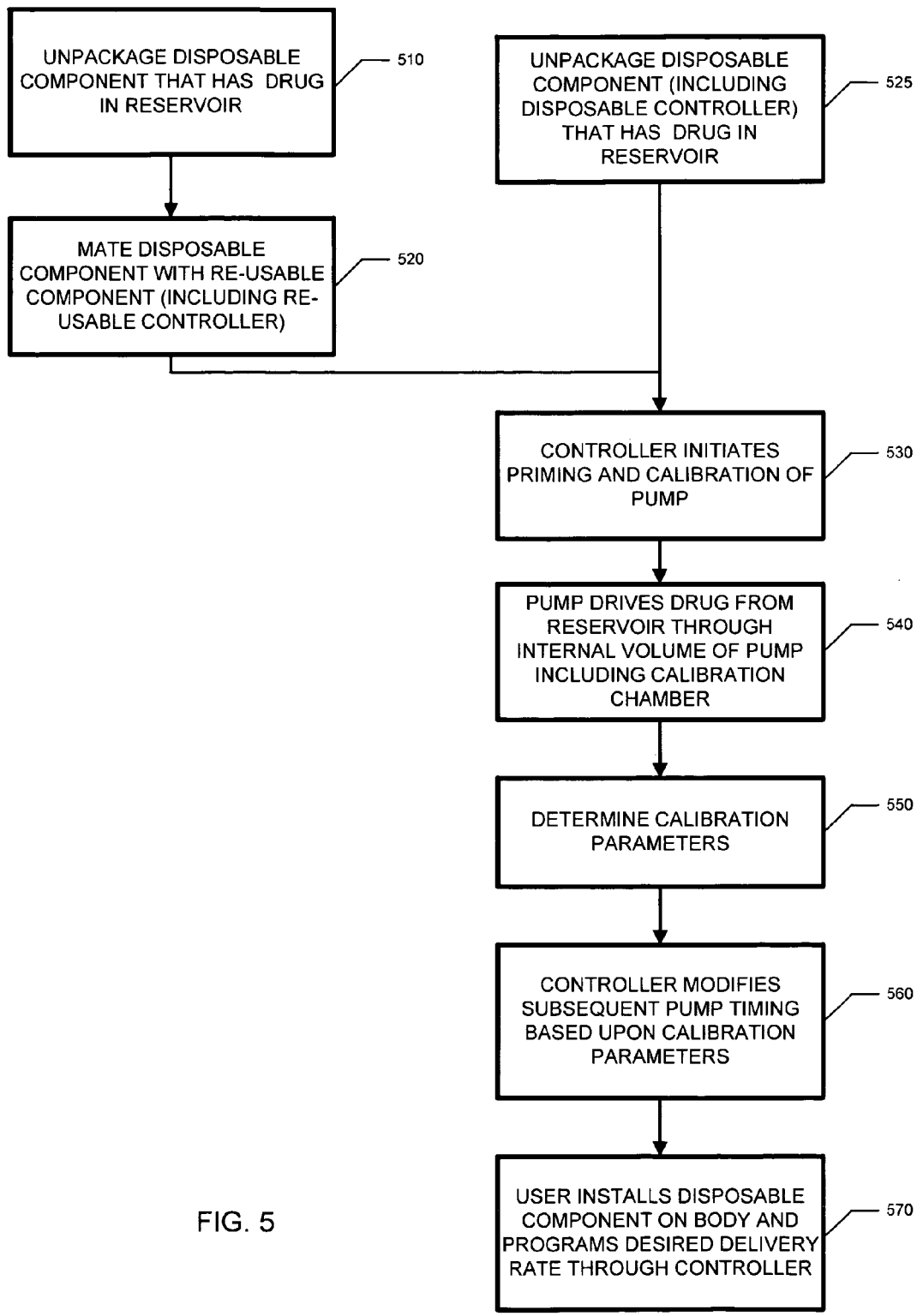
FIG. 5 is a flow chart of operation according to an embodiment of the present invention.

FIG. 5 is a flowchart depicting usage of two embodiments of the system. One embodiment comprises two units, a disposable unit and a re-usable unit, whereas the other embodiment incorporates all the components into one disposable unit. Some or all of the parts of the system shown in FIG. 1B may be reusable, but in the case where there exists a reusable component, it comprises control unit 150. The term disposable refers to the ordinary meaning of the word, and is involves intended usage on the order of days to months. The term reusable also refers to the ordinary meaning and describes a durable component with an intended usage on the order of months to years.

In step 510, the user unpackages the disposable component that has a selected liquid or drug in a reservoir. Next, in step 520, the user mates the disposable component with the re-usable component.

Alternatively, the user simply unpackages the system (pre-loaded with the liquid in the reservoir), which is entirely disposable, in step 525.

Thereafter, the controller initiates priming and calibration of the pump in step 530. In step 540, the pump then drives the liquid from the reservoir through the internal volume of the pump, including through calibration region 154. Next in step 550, calibration parameters, such as the calibration factor are determined. Thereafter, in step 560, the controller modifies the subsequent pump timing based upon the calibration parameters. For instance, if the calibration parameters indicate the measured volume of a particular pump is less than the expected nominal volume of production units, the dosage frequency will be increased. In step 570, the user installs the disposable component (including the controller in one embodiment) and programs the desired delivery rate through the controller user interface. Step 560 may occur before or after step 570, and there is no particular order of the steps unless explicitly stated.

Experimental Results

An embodiment of the present invention was tested in three trials. The dose volume was determined with the embodiment and compared to a gravimetric determination of the dose volume. The results confirm the accuracy of measurements made with the embodiment. The results of three measurements are shown below.

A functional model of the calibration device of the present invention was constructed of a length of tubing with an outer diameter of 0.125 inches and an inner diameter of 0.0625 inches. The sensors were pairs of copper wire and electrical continuity between the two wires of a given pair was measured as an indication of wetting by insulin. A small voltage was applied between each of the sensor electrode pairs. At the point at which the leading edge of the advancing insulin contacted either of the sensor electrode pairs, a circuit was completed resulting in the flow of current through the circuit. This current flow was detected by monitoring the voltage across a current sensing resistor placed in each sensor circuit. The time required for the leading edge of the advancing insulin to traverse the distance between the two sensors was monitored with a timing device.

As can be seen below, three trial measurements were consistent to within 1% and agreed with the two gravimetric measurements to within 1%. The two gravimetric measurements agreed to within 2%. The measurement made with the functional model is approximately the average of the two gravimetric measurements. This confirms the accuracy of the present invention.

| Test Calibration Region | |
|---|---|
| ID: | 1.588 mm (0.0625") |
| Cross sectional area: | 1.979 mm$^2$ |
| Electrode spacing: | 76.20 mm (3.00") |
| Volume: | 150.80 mm$^3$ |
| Trial 1 | |
| Dose period: | 14.92 seconds |
| Time to traverse electrodes: | 1003 seconds |
| Doses to traverse electrodes: | 67 (rounded to nearest whole) |
| Dose volume: | 2.251 mm$^3$ |
| Measured dose volume (gravimetric): | 188.47 mg/83 doses = 2.271 mg/dose |
| Ratio: | 0.99 |
| Trial 2 | |
| Dose period: | 14.92 seconds |
| Time to traverse electrodes: | 996 seconds |
| Doses to traverse electrodes: | 67 (rounded to the nearest whole) |
| Dose volume: | 2.251 mm$^3$ |
| Measured dose volume (gravimetric): | N/A |
| Ratio: | N/A |
| Trial 3 | |
| Dose period: | 14.92 seconds |
| Time to traverse electrodes: | 995 seconds |
| Doses to traverse electrodes: | 67 (rounded to nearest whole) |
| Dose volume: | 2.251 mm$^3$ |
| Measured dose volume (gravimetric): | 184.64 mg/83 doses = 2.225 mg/dose |
| Ratio: | 0.99 |

Although the various aspects of the present invention have been described with respect to exemplary embodiments thereof, it will be understood that the present invention is entitled to protection within the full scope of the appended claims.

The invention claimed is:

1. A method, comprising:
    initiating pumping of at least one dose using, at least in part, a shape memory element, wherein the shape memory element is operatively coupled to a piston and is configured to move the piston between a plurality of positions within a first portion of the pumping mechanism when pumping the at least one dose;
    measuring the at least one dose by monitoring the time it takes the at least one dose to pass from a first sensor to a second sensor, wherein measuring the at least one dose includes determining a flow characteristic of the at least one dose;
    comparing the measured at least one dose to an expected value of the at least one dose;
    calculating a ratio based on the comparing the measured at least one dose to the expected value of the at least one dose;
    applying the calculated ratio to at least one subsequent dose when delivering the at least one subsequent dose; and
    adjusting a flow rate of the at least one subsequent dose when delivering the subsequent dose based at least in part on the determined flow characteristic.

2. The method of claim 1, further comprising modifying a frequency of dosage delivery based on comparing the measured at least one dose to the expected value of the at least one dose.

3. The method of claim 1, wherein the at least one dose is an insulin dose.

4. The method of claim 1, including modifying the pumping of the at least one dose based at least in part on the comparing the measured at least one dose to the expected value of the at least one dose.

5. The method of claim 1, wherein measuring the at least one dose further comprises determining a flow rate of the at least one dose.

6. The method of claim 5, wherein the flow characteristic of the at least one dose corresponds to a voltage of a reaction rate associated with a component of a liquid of the at least one dose.

7. The method of claim 1, including providing one or more feedback control signals to a control unit based, at least in part, on the measured at least one dose.

8. The method of claim 7, wherein the one or more feedback control signals includes a measured volume of the at least one dose, or a measured time duration of the at least one dose.

9. An apparatus, comprising:
    a data communication interface;
    one or more processors operatively coupled to the data communication interface; and
    a memory storing instructions which, when executed by the one or more processors, causes the one or more processors to initiate pumping of at least one dose using, at least in part, a shape memory element, wherein the shape memory element is operatively coupled to a piston and is configured to move the piston between a plurality of positions within a first portion of the pumping mechanism when pumping the at least one dose, measure the at least one dose by monitoring the time it takes the at least one dose to pass from a first sensor to a second sensor, wherein measuring the at least one dose includes determining a flow characteristic of the at least one dose, compare the measured at least one dose to an expected value of the at least one dose, calculate a ratio based on the comparing the measured at least one dose to the expected value of the at least one dose, apply the calculated ratio to at least one subsequent dose when delivering the at least one subsequent dose, and adjust a flow rate of the at least one subsequent dose when delivering the subsequent dose based at least in part on the determined flow characteristic.

10. The apparatus of claim 9, wherein the at least one dose is an insulin dose.

11. The apparatus of claim 9, wherein the memory storing instructions which, when executed by the one or more processors, further causes the one or more processors to modify the pumping of the at least one dose based at least in part on the comparing the measured at least one dose to the expected value of the at least one dose.

12. The apparatus of claim 9, wherein the memory storing instructions which, when executed by the one or more processors, further causes the one or more processors to provide one or more feedback control signals to a control unit based, at least in part, on the measured at least one dose.

13. The apparatus of claim 12, wherein the one or more feedback control signals includes a measured volume of the at least one dose, or a measured time duration of the at least one dose.

14. The apparatus of claim 9, wherein the memory storing instructions which, when executed by the one or more processors, further causes the one or more processors to modify a frequency of dosage delivery based on comparing the measured at least one dose to the expected value of the at least one dose.

15. The apparatus of claim 14, wherein the measurement of the at least one dose further comprises a determination of a flow rate of the at least one dose.

16. The apparatus of claim 15, wherein the flow characteristic of the at least one dose corresponds to a voltage of a reaction rate associated with a component of a liquid of the at least one dose.

* * * * *

UNITED STATES PATENT AND TRADEMARK OFFICE
CERTIFICATE OF CORRECTION

PATENT NO. : 8,343,093 B2
APPLICATION NO. : 12/790733
DATED : January 1, 2013
INVENTOR(S) : Benjamin M. Rush Page 1 of 1

It is certified that error appears in the above-identified patent and that said Letters Patent is hereby corrected as shown below:

Title Page:
Section (60), replace "60/417,434" with --60/417,464--

Signed and Sealed this
Nineteenth Day of February, 2013

Teresa Stanek Rea
*Acting Director of the United States Patent and Trademark Office*